US012776407B2

(12) United States Patent
Koerner et al.

(10) Patent No.: US 12,776,407 B2
(45) Date of Patent: Oct. 27, 2026

(54) SYSTEM FOR DYNAMICALLY ANALYZING AND IMPROVING PHYSICAL PERFORMANCE AND INJURY MITIGATION IN TACTICAL PERFORMERS

(71) Applicant: United States Performance Center, LLC, Charlotte, NC (US)

(72) Inventors: David Joseph Koerner, Charlotte, NC (US); Irwin Belk, II, Charlotte, NC (US)

(73) Assignee: United States Performance Center, LLC, Charlotte, NC (US)

(*) Notice: Subject to any disclaimer, the term of this patent is extended or adjusted under 35 U.S.C. 154(b) by 192 days.

(21) Appl. No.: 18/649,210

(22) Filed: Apr. 29, 2024

(65) Prior Publication Data

US 2024/0331832 A1 Oct. 3, 2024

Related U.S. Application Data

(63) Continuation-in-part of application No. 18/581,242, filed on Feb. 19, 2024.

(Continued)

(51) Int. Cl.

*G16H 20/30* (2018.01)
*A63B 24/00* (2006.01)

(Continued)

(52) U.S. Cl.

CPC ......... *G16H 20/30* (2018.01); *A63B 24/0062* (2013.01); *G16H 10/60* (2018.01); *A63B 2071/0652* (2013.01)

(58) Field of Classification Search

CPC .... G16H 20/30; G16H 10/60; A63B 24/0062; A63B 2071/0652; A63B 21/4035;

(Continued)

(56) References Cited

U.S. PATENT DOCUMENTS 5,260,870 A * 11/1993 Tsuchiya .............. A63B 21/153 600/595
5,277,674 A * 1/1994 Tsuchiya .............. A63B 21/153 600/595

(Continued)

OTHER PUBLICATIONS

Force-Velocity-Power Profile Characteristics, excerpt from NSCA's Essentials of Sport Science, 2022, accessed Nov. 7, 2025 https://www.nsca.com/education/articles/kinetic-select/force-velocity-power-profile-characteristics/?srsltid=AfmBOopD-nkE4rb3qcXYoR7_kVDc6BpLULJqzTg3sel9UEkyFpUEah70# (Year: 2022).*

*Primary Examiner* — Sundhara M Ganesan
(74) *Attorney, Agent, or Firm* — Kim and Lahey Law Firm, LLC; Douglas W. Kim

(57) ABSTRACT

This system can be a combination of hardware and equipment, software, training methodologies, data feedback loops and methods of instruction and activity so that target individual such tactical athletes' (e.g., military, law enforcement, firefighters, first responders, and the like) performance can be improved through following this integrative performance training system. This system involves evaluations and individualized training prescriptions that are automatically and continuously modified according to changes in the individual's performance measures. This system also includes assistance and instructions that can accompany training allow for biofeedback to be used to maximize neuromuscular performance during each session. In one embodiment, individualized performance training system can meet the target individual at their current ability levels and specifically target deficits to improve performance outcomes. In one embodiment, individualized performance training system can meet the target individual mission performance goals.

20 Claims, 13 Drawing Sheets

Related U.S. Application Data

(60) Provisional application No. 63/619,370, filed on Jan. 10, 2024, provisional application No. 63/512,415, filed on Jul. 7, 2023, provisional application No. 63/499,217, filed on Apr. 29, 2023, provisional application No. 63/485,891, filed on Feb. 18, 2023.

(51) Int. Cl.
*A63B 71/06* (2006.01)
*G16H 10/60* (2018.01)

(58) Field of Classification Search
CPC ........ A63B 24/0087; A63B 2024/0093; A63B 2220/30; A63B 2220/51; A63B 2225/50
See application file for complete search history.

(56) References Cited

U.S. PATENT DOCUMENTS 5,993,356 A * 11/1999 Houston ............ A63B 21/0058 482/7
6,430,997 B1 * 8/2002 French .................... A63F 13/45 73/379.04
6,450,967 B1 * 9/2002 Wu ........................ A63B 22/00 600/500
9,693,727 B1 * 7/2017 Saalasti ................ A61B 5/4866
11,154,752 B2 * 10/2021 Azaria ............... A63B 71/0622
11,596,837 B1 * 3/2023 Belson ............... A63B 24/0087
11,745,039 B2 * 9/2023 Peal ................... A63B 21/0059 482/5
12,186,627 B2 * 1/2025 Cei .................... A63B 22/0605
2008/0242512 A1 * 10/2008 Kim ..................... A63B 21/065 482/8
2008/0261776 A1 * 10/2008 Skiba ................. A63B 24/0006 482/8
2010/0069202 A1 * 3/2010 Olsen ................. A63B 21/0058 482/92
2011/0082006 A1 * 4/2011 Ishii ................... A63B 21/0058 482/5
2011/0294624 A1 * 12/2011 Burnfield ......... A63B 21/00181 482/145
2012/0142497 A1 * 6/2012 Ishii ................... A63B 21/0056 482/4
2014/0274565 A1 * 9/2014 Boyette .............. A63B 22/0694 482/6
2015/0375045 A1 * 12/2015 Ojanen .............. A63B 21/0023 482/5
2016/0114211 A1 * 4/2016 Schmidt ............. A63B 21/4043 482/8
2017/0189752 A1 * 7/2017 Mohrman ............ A61B 5/4866
2017/0361165 A1 * 12/2017 Miller ................ A63B 21/4047
2017/0361166 A1 * 12/2017 Hong ................... A63B 21/153
2018/0296879 A1 * 10/2018 Blium ................ A63B 21/0615
2019/0001184 A1 * 1/2019 Schindler-Ivens ........................... A63B 22/0605
2019/0192906 A1 * 6/2019 Smith ................ A63B 71/0622
2019/0290958 A1 * 9/2019 Shahriar ............ A63B 21/4033
2019/0344123 A1 * 11/2019 Rubin .................. A63B 21/153
2020/0086197 A1 * 3/2020 Kim ................... A63B 23/1218
2020/0289880 A1 * 9/2020 Hacking ............ A63B 22/0664
2020/0360764 A1 * 11/2020 Smith .............. A63B 21/00178
2020/0384342 A1 * 12/2020 Nakashima ........ A63B 22/0023
2021/0031091 A1 * 2/2021 Glidden ............. A63B 71/0622
2021/0252340 A1 * 8/2021 Smith ................ A63B 24/0062
2022/0016484 A1 * 1/2022 Bissonnette ....... A63B 23/0417
2022/0047921 A1 * 2/2022 Bissonnette ....... A63B 24/0006
2022/0126169 A1 * 4/2022 Mason ............... A63B 24/0062
2022/0134186 A1 * 5/2022 Zoffoli ............. A63B 21/00181 482/4
2022/0288460 A1 * 9/2022 Mason ................. A61B 5/1071
2022/0370851 A1 * 11/2022 Guidarelli .......... A63B 24/0075
2022/0401794 A1 * 12/2022 Bissonnette ........... G06N 20/00
2023/0058605 A1 * 2/2023 Mason ................... G16H 50/70
2023/0072368 A1 * 3/2023 Mason ............... A63B 24/0087
2023/0115911 A1 * 4/2023 Keiser .................. A61B 5/1121 600/595
2023/0124164 A1 * 4/2023 Zoffoli ............... A63B 24/0087 482/5
2023/0245747 A1 * 8/2023 Rosenberg ............. G16H 50/30 705/3
2023/0253089 A1 * 8/2023 Rosenberg ......... A63B 24/0087 705/3
2023/0321492 A1 * 10/2023 Zoffoli ............... A63B 24/0006 482/8
2023/0377711 A1 * 11/2023 Rosenberg ......... A63B 24/0062
2023/0377712 A1 * 11/2023 Rosenberg ............. G16H 15/00
2023/0381592 A1 * 11/2023 Ellzey ................ A63B 71/0622
2024/0024731 A1 * 1/2024 Rosenberg ......... A63B 71/0622
2024/0062869 A1 * 2/2024 Rosenberg ......... A63B 22/0605
2024/0062870 A1 * 2/2024 Rosenberg ......... A63B 22/0605
2024/0136041 A1 * 4/2024 Rosenberg ............. G16H 20/30
2024/0266022 A1 * 8/2024 Rosenberg ....... A63B 21/00181
2025/0205557 A1 * 6/2025 Mason ................... G16H 10/60

* cited by examiner

SYSTEM FOR DYNAMICALLY ANALYZING AND IMPROVING PHYSICAL PERFORMANCE AND INJURY MITIGATION IN TACTICAL PERFORMERS

RELATED APPLICATIONS

This application is a non-provisional patent application claiming priority from U.S. Patent Application 63/619,370 filed Feb. 20, 2024; 63/512,415 filed Jul. 7, 2023 and 63/499,217 filed Apr. 29, 2023. This application is a continuation in part of U.S. patent application Ser. No. 18/581,242 filed Feb. 20, 2024 which is a non-provisional application from 63/485,891 filed Feb. 18, 2023.

BACKGROUND OF THE INVENTION

1) Field of the Invention

This invention is directed to a system and method of dynamically measuring, determining, modifying, and implementing a schema for improving physical performance, reducing injury risk and/or rehabilitating a musculoskeletal injury in certain members of the population that seek improvement in physical performance. More specifically, improving physical performance, reducing injury risk and/or rehabilitating musculoskeletal injury in war fighters and first responders. The system can be used for measuring, managing, and improving physical performance for tactical athletes such as military, first responders, and the like.

2) Description of the Related Art

America's military and first responders must be able to perform at the highest levels in order to successfully complete the mission at hand. Considerable resources are put into the training of the first responder and warfighters. For example, it is reported that over one and one half million dollars and over a year is spent to train special forces soldiers. Even the very initial training is an investment and estimated to be as much as $75,000. Therefore, there is a need to have these individuals at peak physical performance and to provide fast recovery times when one is injured. Further, the ability to improve physical performance during the service of these individuals is a benefit.

The military's current approach to physical readiness practices (Human Performance Optimization and Injury Prevention) have only recently begun to address strength and power performance, in training and doctrine. Studies have shown that the incorporation of resistance training provides superior gains in strength, power, muscle hypertrophy, and military task performance when compared to conventional military field training. In addition, the US Military experiences high rates of musculoskeletal injuries (MSI) which has led to billions of dollars in cost and thousands of soldiers non-deployable. Some MSI can be career ending. The current invention can be used to repair MSI as well as to reduce the risk associated with MSI. This benefit can lead to an increase in strength and power production for the target individual and can be included in individualized training.

It would be advantageous to have a system that can analyze, improve, enhance and manage physical performance for tactical athletes.

It would also be advantageous to have a system that can detect and mitigate potential and actual injuries.

It would also be advantageous to have a system that can assist with matching physical performance of tactical athletes with mission requirements for both training and live missions.

BRIEF SUMMARY OF THE INVENTION

The above objectives can be accomplished by providing a system for dynamically implementing a physical performance evaluation improvement and rehabilitative schema that can applied to and benefit a target individual such as a first responder, warfighter (e.g., soldier), tactical athlete, and the like. The system can include an exercise machine having a load assembly for applying a load to a limb of a target individual; a force/load sensor for determining the force/load applied to the limb as the target individual uses the exercise machine; a velocity sensor for receiving velocity information representing the force applied to the load by the target individual; and, computer system in communications with the sensors for determining power, receiving load information, receiving velocity information and determining modifications in the load applied to the target individual.

The system can include computer readable instructions that can receive information about the biomechanics and performance of the athletes in light of the training program, determine the improvements or changes in the athletes biomechanics and performance, use trends, machine learning, algorithms, and other data analysis to propose or make modifications to the training programs thereby providing a feedback mechanism to assist with improving the training program and the athlete's outcome.

The computer readable instructions can determine measures for maximal strength, peak power, and power velocity and compare measurements between limbs. The computer readable instructions can determine an initial status of the target individuals, an initial workout scheme according to the data received from the sensors and subsequently modify that workout scheme according to the data received from the sensors. The target can be for maintenance of existing physical performance, improvement of physical performance, rehabilitation from an injury, or any combination. For example, a soldier may wish to change their status from civilian to military or military to special operations and need to improve fitness to reach these goals. The system can set customized and personalized targets based upon the current physical fitness of the target individual and the ultimate goal of that individual. The system can specifically target the areas of deficit noted by the assessment process. The system allows the target individual to maintain and improve a combination of strength, power, and grip; speed and agility; muscle stamina and endurance, and flexibility and mobility.

The system allows for competing goals to be managed. For example, a target for one individual may be strength, therefore the system has programming and feedback accordingly. Another individual may wish to accomplish longer running events. Yet another individual may wish to train for a specific mission. One mission may require long hikes which require stamina while another mission may require carrying heavy loads, but shorter distances. The system has the ability to assist team leaders with team selection duties to pick individuals with physical performance levels that meet the mission standards.

The workout scheme can be determined using an iterative process from data from the recent workouts. The computer readable instructions can be adapted for receiving load information, receiving velocity information, and determining modifications to the load applied to the target individual.

The workout scheme can be determined according to the data received from the sensors and a target individual's characteristics. The computer readable instructions can determine a workout scheme according to the data received from the sensors and a dataset of prior target individual characteristics as well as wherein the target individual characteristics match those of another target individual characteristics in the dataset.

The system implementing a dynamic performance enhancing schema comprising can include an exercise machine having a load assembly for applying a load to a limb of a target individual; a force sensor in electrical communications with the load assembly for detecting a force applied by the limb by the target individual using the exercise machine; a velocity sensor for receiving velocity information representing a velocity applied by the limb by the target individual using the exercise machine; and, a computer system in communications with the load assembly, the force sensor and the velocity sensor for determining power output, receiving load information, receiving velocity information, receiving force information, determining a power curve and velocity relationship, modifying the load applied to the target individual according to the power and velocity relationship and applying the modified load to the limb of the target individual during a subsequent use of the exercise machine by the target individual.

The limb can be a first limb, the force sensor can be a first force sensor, the velocity sensor can be a first velocity sensor and the power output can be a first power output and the computer system can be adapted to create a work scheme for a second limb according to a second power output derived from a second force sensor and a second velocity sensor. The computer system can be adapted to determine a performance target according to historical performance information of the target individual according to the power and velocity data, determine a performance target according to a set of mission parameters, determine a target according to a set of historical mission parameters, determine a target individual performance goal according to an individual performance goal.

The target individual performance goal can be a performance standard. The computer system can be adapted to determine an estimated maximal load, determine a peak power and power velocity, determine a workout scheme according to the power information, the load information, the velocity information, the force information, the relationship between power and velocity and a performance target.

The power information can be a first power information, the load information is a first load information, the velocity information is a first velocity information, the force information is a first force information and the computer system if adapted to create modifications to according to a second power information, a second load information, a second velocity information, and a second force information received from a subsequent use of the exercise machine by the target individual.

The system computer system can be adapted to determine a workout scheme using an iterative process from a set of load information, a set of velocity information, and a set of force information, and a set of power information received from the subsequent use of the exercise machine by the target individual. The computer system can be adapted to determine whether modifications in the load applied to the target individual are repeated for each target individual session.

The can include a set of prior user characteristics; a computer system adapted to receive a set of target individual characteristics and generate an initial workout scheme according to a similarity match of the target individual characteristics and the set of prior user characteristics; an exercise machine having a load assembly for applying a load to a limb of a target individual according to the initial workout scheme; a force sensor in electrical communications with the load assembly for detecting a force applied by the limb by the target individual using the exercise machine; a velocity sensor for receiving velocity information representing a velocity applied by the limb by the target individual using the exercise machine; and, wherein the computer system is in communications with the load assembly, the force sensor and the velocity sensor and adapted for determining power output, receiving load information, receiving velocity information, receiving force information, determining a power and velocity relationship, creating a modified workout scheme according to the power and velocity relationship.

The modified workout scheme can include a modified load applied to the limb of the target individual during a subsequent use of the exercise machine by the target individual. The computer system can be adapted to create a work scheme for a second limb according to a second power dataset derived from a second force sensor, second velocity sensor, and second applied load, create the workout scheme for a second limb according to workout scheme of the first limb.

The system can include a computer system adapted to receive a set of target individual characteristics and generate an initial workout scheme according to a set of mission performance parameters; an exercise machine having a load assembly for applying a load to a limb of a target individual according to the initial workout scheme; a force sensor in electrical communications with the load assembly for detecting a force applied by the limb by the target individual using the exercise machine; a velocity sensor for receiving velocity information representing a velocity applied by the limb by the target individual using the exercise machine; and, wherein the computer system is in communications with the load assembly, the force sensor and the velocity sensor and adapted for determining power information, receiving load information, receiving velocity information, receiving force information, determining a power and velocity relationship, creating a modified workout scheme according to the power velocity curve.

The computer system can be adapted to generate a second initial workout scheme for a second limb and generate a second power and velocity relationship for the second limb and determine a difference between the first power and velocity relationship and the second power and velocity relationship indicating a difference in performance between bilateral limbs.

BRIEF DESCRIPTION OF THE SEVERAL VIEWS OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein.

DETAILED DESCRIPTION OF THE INVENTION

With reference to the drawings, the invention will now be described in more detail. This system can be a combination of hardware and equipment, software, training methodologies, data feedback loops and methods of instruction and activity so that the exercise training can be targeted and, in one embodiment, can be automatically adjusted based on the needs of an individual target individual. This system also includes assistance and instructions that can accompany biofeedback training for maximal voluntary activation of the nervous system to promote greater physical improvements. This system can also train involuntary activation by incorporating electrical or magnetic stimulation as necessary. In one embodiment, this system is not passive, but rather directly targets the nervous system to meet the target individual at their current ability levels.

Figure 1:
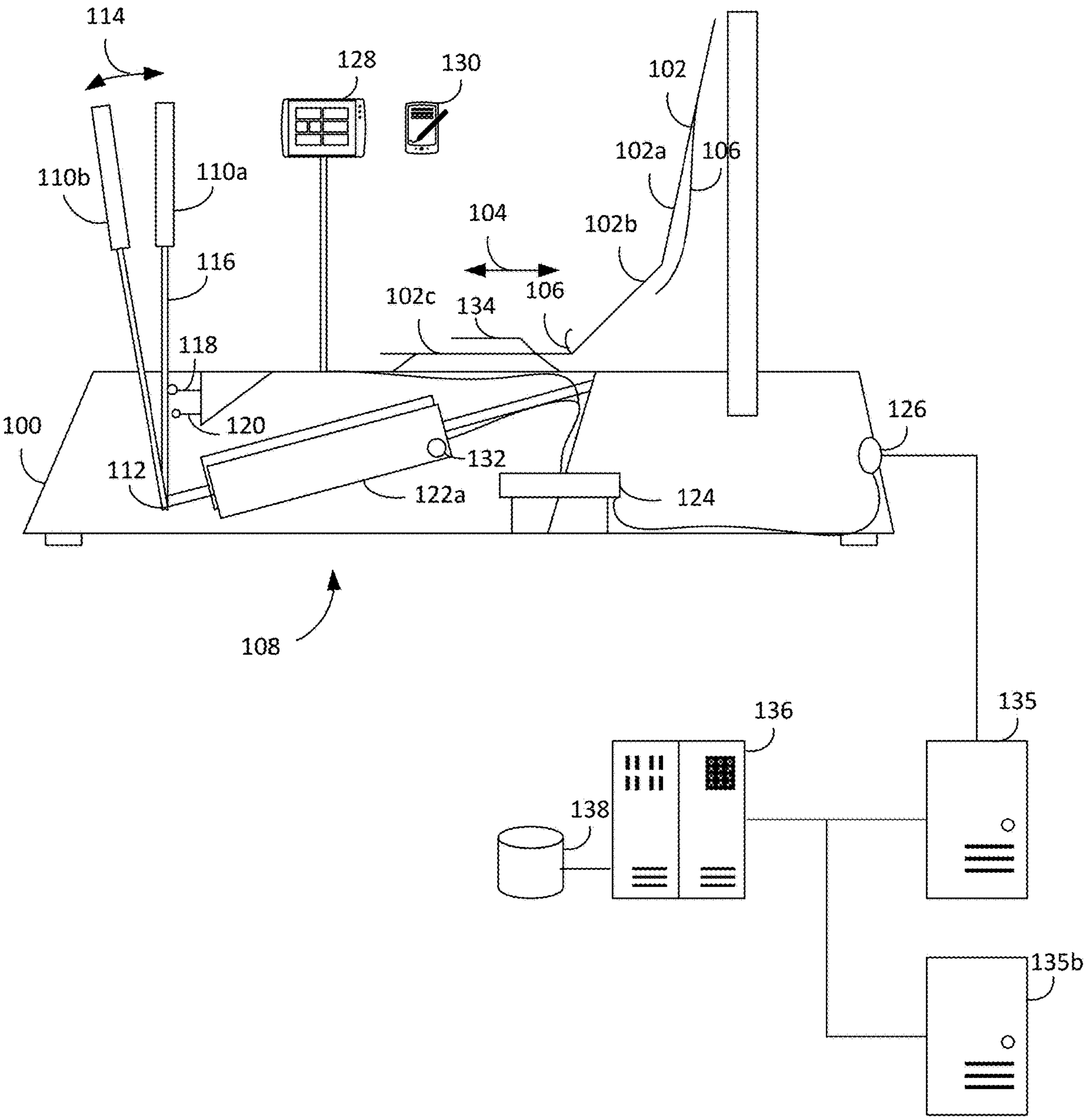
FIG. 1 is a schematic of a machine that can be used with the system.

Referring to FIG. 1, exemplary fitness equipment is shown having a base 100 that can support a seating assembly 102. The seating assembly can support a target individual and can be positioned along path 104 for consideration of varying torso length, leg lengths and overall heights of the target individual. In one embodiment, the seat can have section 102*a* through 102*c* that can be rotated relative to each other to change the sitting angle of the target individual. The seat or frame can include security straps 106 or other security assembly (e.g., straps, bars) to secure the target individual into the seat and prevent unintentional falling or other motion in the seat.

The frame can include a resistance assembly 108 that can, in this embodiment, can be connected to a foot pedal 110*a* wherein the foot pedal is configured to move along a pivot 112 allowing the target individual's foot to travel along path 114. The frame can carry a second foot pedal 110*b* allowing for independent movement between the first foot pedal 110*a* and the second foot pedal 110*b* allowing for unilateral and bilateral movement of the target individual's feet and legs. The foot pedal can include a foot pedal shaft 116 that can contact a first stop 118 so that the initial position of the foot pedal away from the target individual can be adjusted. Each pedal can connect to a second stop 120 so that there is a minimum distance that the foot pedal can be from the target individual preventing the foot pedal from over traveling toward the target individual.

A load assembly 122*a* can be connected to the first foot pedal or each pedal. The load assembly can be a variable load assembly so that the resistance provided to the target individual can be varied by the variable load assembly. The load assembly can be set to a specific value or can have a graduating value according to factors such as the speed the target individual applies to pressing the load, the number of repetitions in a particulate period of time, reversal strength, deceleration, and the like. The load assembly can include a controller 124 that can vary the load of the load assembly. The load can be varied automatically with computer readable instructions on the controller, information received from a communications port 126 or input from an input device such as a keyboard, touch screen 128 or portable device 130 in communications with the controller. The load assembly can be an air cylinder, motor, fly wheel with variable resistance, transmission, magnetic or electrical resistance, and the like. The load assembly can provide resistance to the foot pedal and therefore the target individual without the impact of gravity. For example, when input is received at the controller, the resistance of the load assembly can vary without consideration of gravity which is in opposition to traditional exercise equipment such as free weights.

The controller can also be connected to one or more sensors 132 that can gather information about the exercise machine and its components, the activities, and the target individual. For example, a sensor can determine the force placed on the foot pedal, the distance that the foot pedal travels, lateral force paced on the foot pedal, the speed in which the foot pedals travels, the acceleration of the foot pedal, repetitions and the like. A sensor can be included in the seat to determine the weight of the target individual and the force against the seat. A sensor can determine the gripping force of the target individual on a handle 134 including forward, rearward, and lateral force placed on the handle. One or more sensors can transmit the information to the controller which can be used to display on a screen 128 or portable device 130. In this example, exercise associated with the lower portion of the body is described. The equipment can be used for one or both legs.

The controller can be connected to server 135, which can be local or remote. The controller can be in communications wirelessly, wired, by local network, wide area network or global communications network. Information can be transmitted to and from the server and the controller. The server can be in communications with an aggregate server 136 and database 138 that can also be in communications with additional servers 135*b*. The controller can include a computer readable medium for data storage, can be in communications with a local or remote data storage system and can include a removable data storage system.

The controller of each machine, or a computer system in communications with the machine, can detect through sensors and display locally or remotely information that includes resistance, force, load, velocity, vectors, acceleration, power, distance, speed, repetitions, range of motion, and the like. The system can measure each of these unilaterally or bilaterally.

Figure 2:
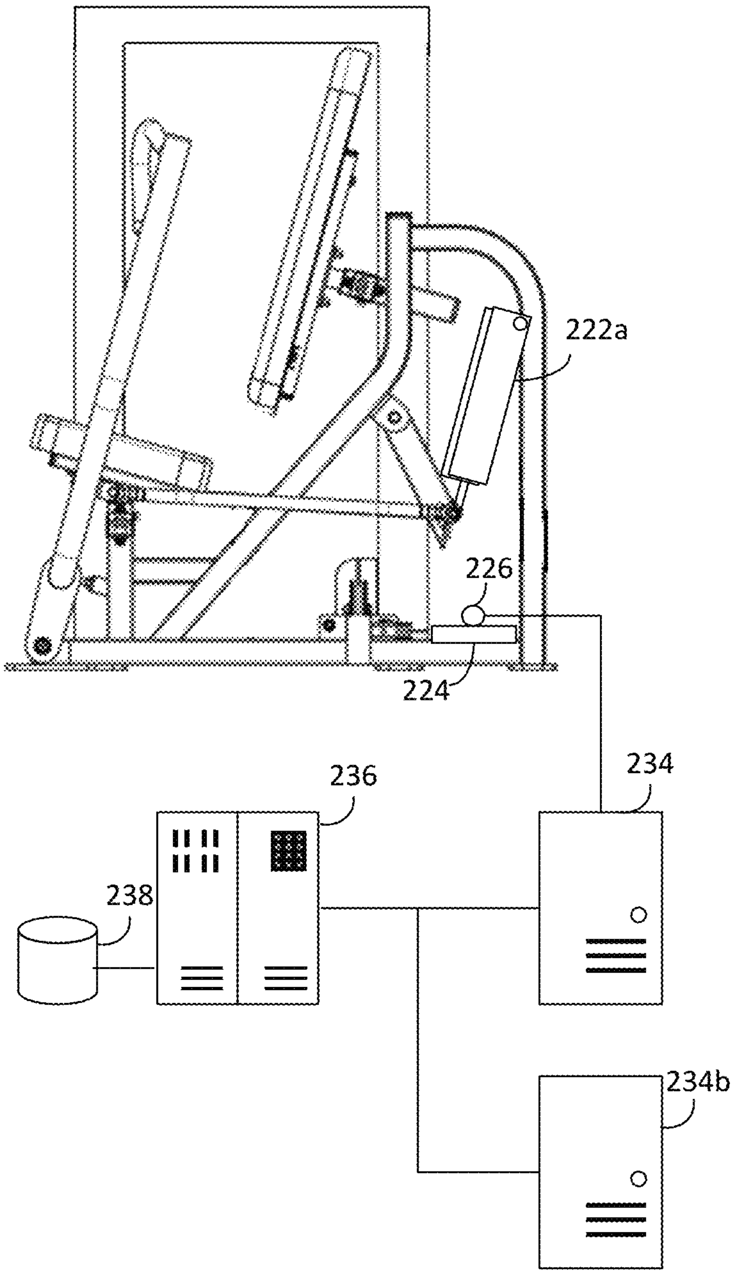
FIG. 2 is a schematic of a machine that can be used with the system.

Referring to FIG. 2, the seated chest press machine is shown. A load assembly 222*a* can be connected to a first chest press bar or each press bar. The load assembly can include a controller 224 that can vary the load of the load assembly. The load can be varied automatically with computer readable instructions on the controller, information received from a communications port 226 or input from an input device such as a keyboard, touch screen or portable device in communications with the controller. The load assembly can be an air cylinder, motor, fly wheel with variable resistance, transmission, magnetic or electrical resistance, and the like. The load assembly can provide resistance to the chest press bar and therefore the target individual without the impact of gravity. For example, when input is received at the controller, the resistance of the load assembly can vary without consideration of gravity which is in opposition to traditional exercise equipment such as free weights. In one embodiment, the equipment can include adjustment to meet the needs of the user, such as seat height, handle positions and the like.

Controller 224 can be connected to server 234. The server can be in communications with an aggregate server 236 and database 238 that can also be in communications with additional servers 234*b*. The controller can include a computer readable medium for data storage, can be in communications with a local or remote data storage system and can include a removable data storage system.

Figure 3:
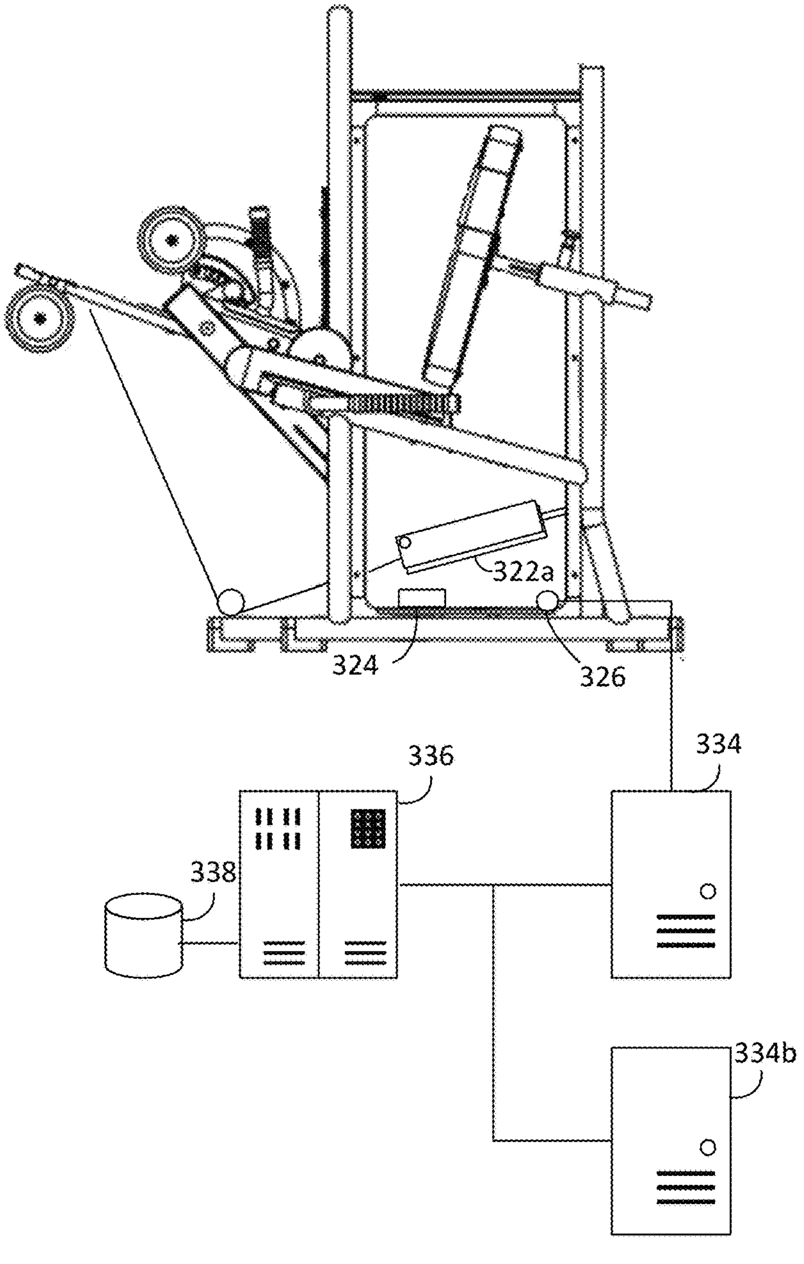
FIG. 3 is a schematic of a machine that can be used with the system.

Referring to FIG. 3, the leg curl machine is shown. The machine can include variations that account for the position of the user, such as sitting and/or prone. The equipment can include adjustments to meet the needs of the user, such as seat height, back pad distance, leg pad settings and the like. A load assembly 322*a* can be connected to a leg curl bar for each lower limb. The load assembly can include a controller 324 that can vary the load of the load assembly. The load can be varied automatically with computer readable instructions on the controller, information received from a communications port 326 or input from an input device such as a keyboard, touch screen or portable device in communications with the controller. Controller 324 can be connected to server 334. The server can be in communications with an aggregate server 336 and database 338 that can also be in communications with additional servers 334*b*. The controller can include a computer readable medium for data storage, can be in communications with a local or remote data storage system and can include a removable data storage system.

Figure 4:
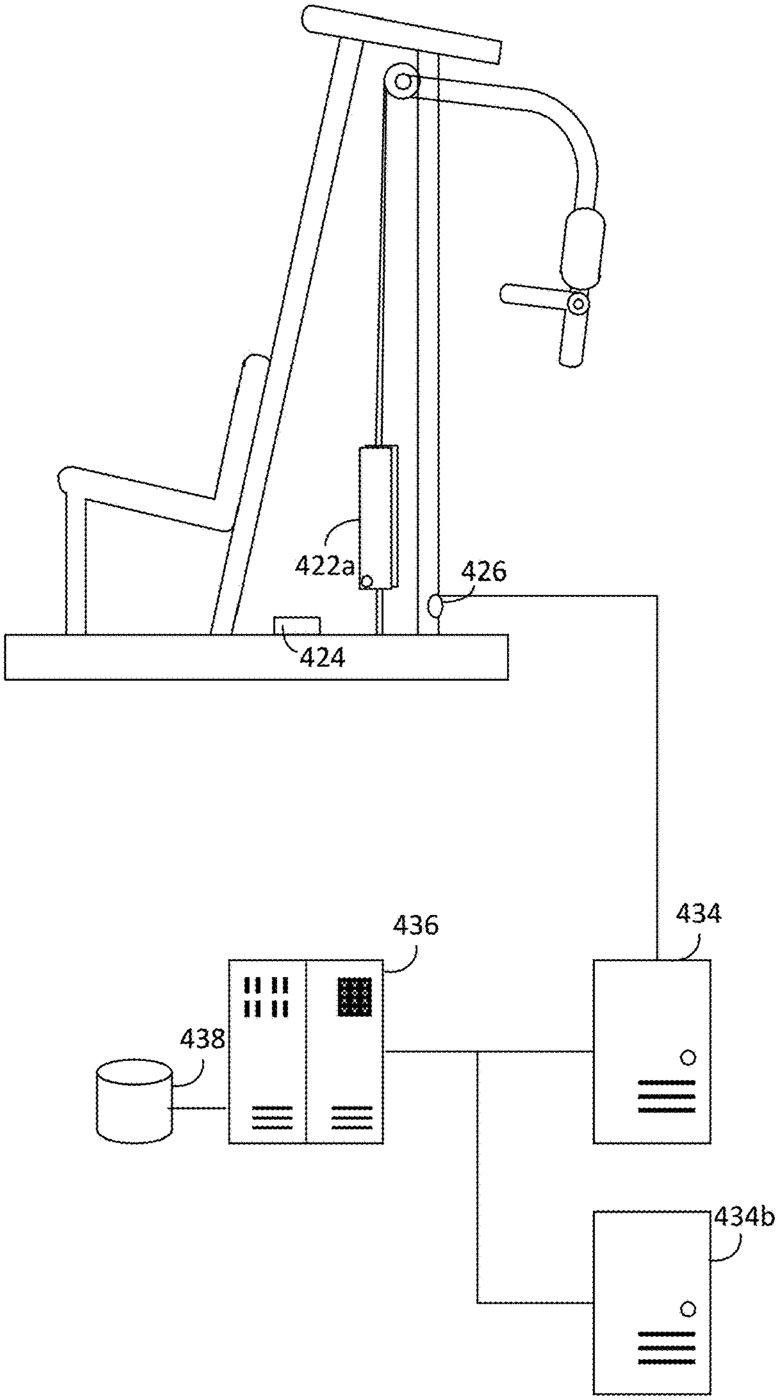
FIG. 4 is a schematic of a machine that can be used with the system.

Referring to FIG. 4, the upper back machine is shown. A load assembly 422*a* can be connected to a pull bar. The equipment can include adjustments to meet the needs of the user, such as seat height, chest pad distance, handle positions and the like. The load assembly can include a controller 424 that can vary the load of the load assembly. The load can be varied automatically with computer readable instructions on the controller, information received from a communications port 426 or input from an input device such as a keyboard, touch screen or portable device in communications with the controller. Controller 424 can be connected to server 434. The server can be in communications with an aggregate server 436 and database 438 that can also be in communications with additional servers 434*b*. The controller can include a computer readable medium for data storage, can be in communications with a local or remote data storage system and can include a removable data storage system.

Figure 5:
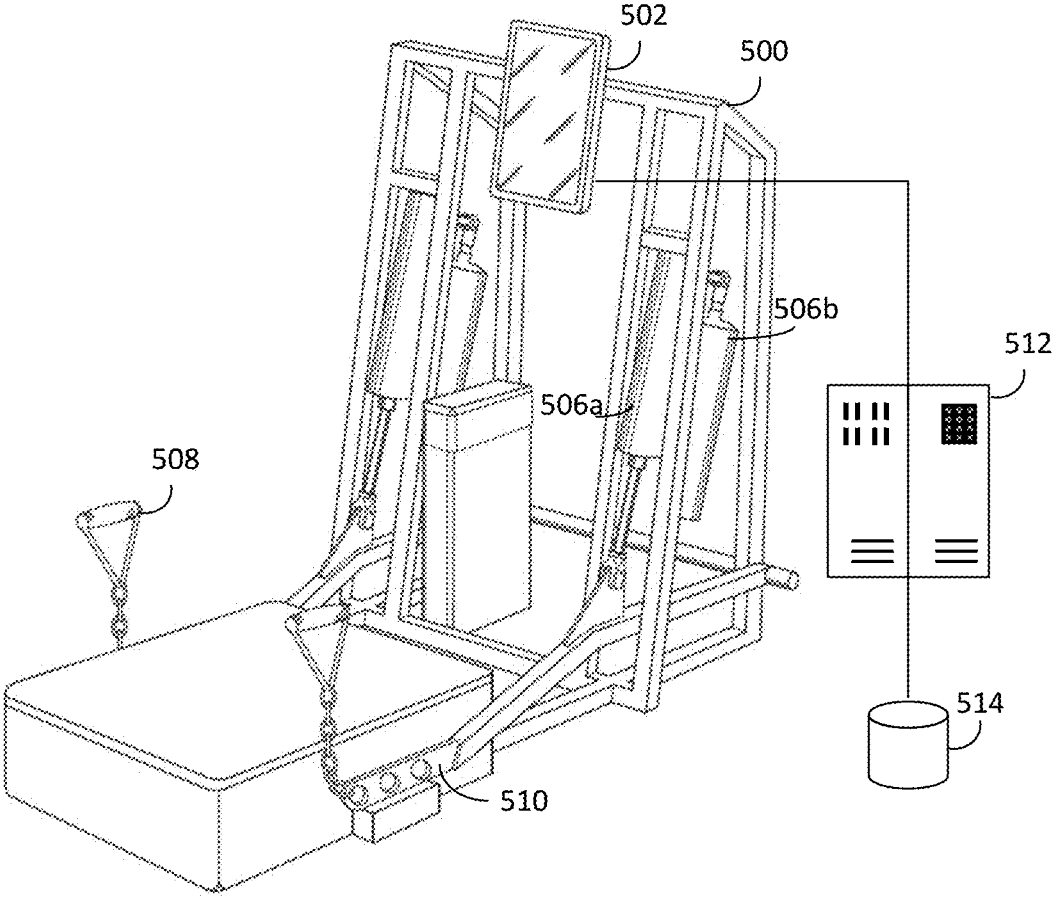
FIG. 5 is a schematic of a machine that can be used with the system.

Referring to FIG. 5, a deadlift machine 500 is shown having a computer device 502 that can receive and transmit information. A touch screen can be included in the computer device. The load (e.g., weight) can be adjusted manually by buttons in one embodiment. The machine can use a set of load assemblies 506*a* and 506*b* (e.g., cylinders) so that the machine can determine the force, speed, and velocity of the target individually bilaterally. In one embodiment the load assemblies can be placed side-by-side, linear arrangement, off-set or another configuration. The load assemblies can provide unilateral and bilateral measurements. The target individual, in one embodiment can use handles 508 that can be pulled upwards, one in each hand. The machine can include a bar 510 where handles can be attached, understanding that it is unlikely that the machine would have the handles and the bar simultaneously. The equipment can include adjustments to meet the needs of the user such as handle height, lever position and the like. The system can transmit and receive information to one or more remote computer systems 512 and storage systems 514.

Figure 6:
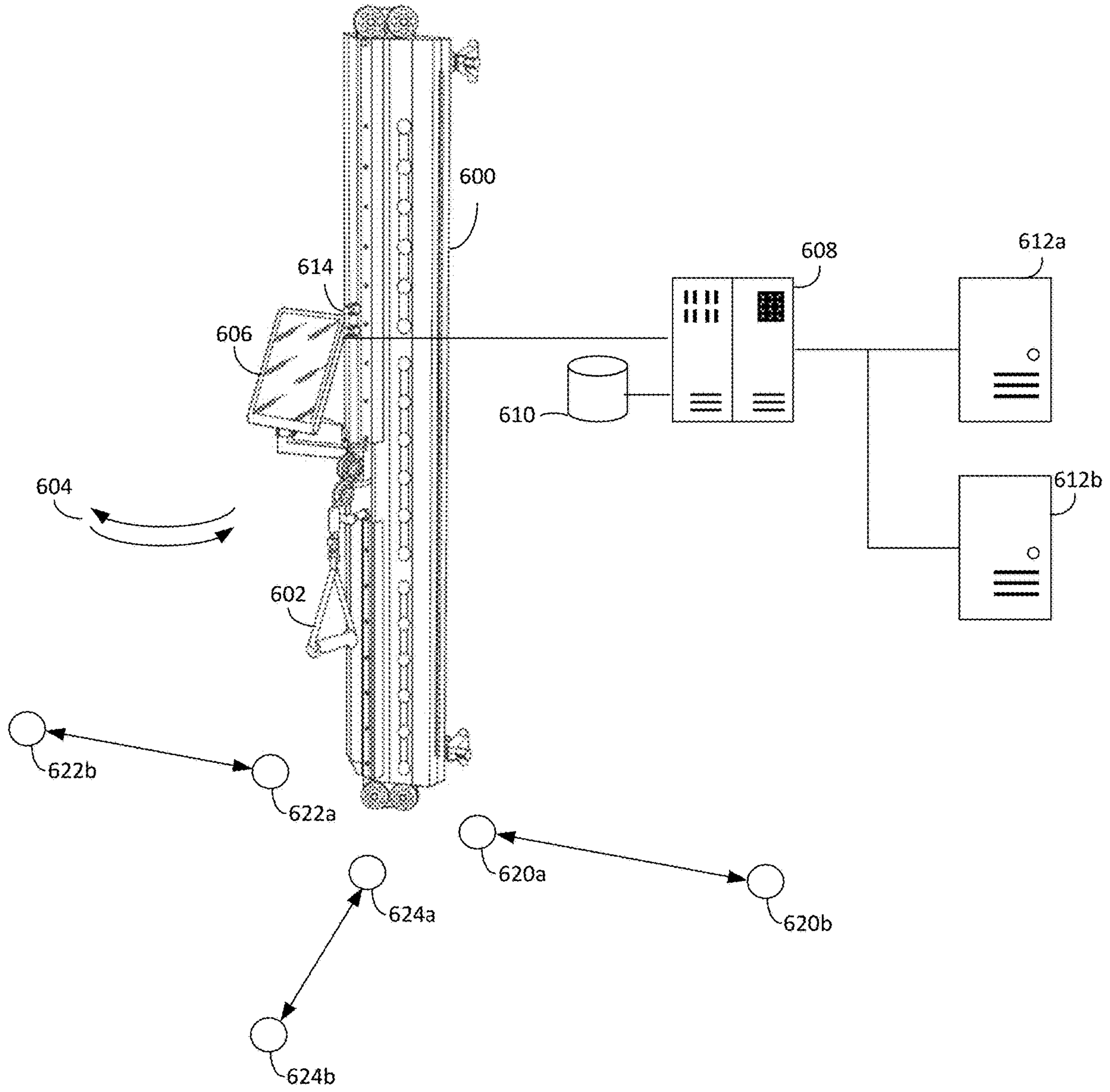
FIG. 6 is a schematic of a machine that can be used with the system.

Referring to FIG. 6, a core rotational machine 600 can be used so that the target individual can provide resistance on handle 602, which can be pulled in any direction, and rotate the target individual body generally in a direction shown as 604, taking measurements in one direction then the other direction for lateral measurements and goal setting. For example, the individual can pull the handle from point 620*a* to 620*b*, 622*a* to 622*b*, 624*a* to 624*b* and any direction wherein the handle can travel. In one embodiment, the range where the handle can extend can be about 270 degrees.

While specific machines are used for illustrative purposes, the invention is not limited to a particular machine or machine configuration. Other machines can be used such as a lat pull down, ergometer, cable biceps, hanging leg raise, seated dip, chest fly, bench press, arm curl, arm extension, triceps press, triceps extension, shoulder press, overhead press, lateral raise, back extension, glute ham developer (GHD) machine, front pull, abdominal crunch, leg extension, rotary torso, hip thrust, squat, seal row, calf raise, cycle, rower and any number of exercise equipment.

In one embodiment, the machines can be affixed to a floor or base or affixed to a wall. The information used by the system can be entered into computer device 606 which can also display information in real time during the use of the machine. The settings can also be provided by a remote computer system 608. Data from the process can be stored on computer readable medium 610 and provided to other systems 612*a* and 612*b* which can aggregate the information.

The data collected can include force, velocity, load, power, acceleration, and the like. The system can use force, velocity, power, set number, repetition number and other data and provide the data to the other systems. The other systems can also be used to provide goals, mission performance requirements, and the like. In one embodiment, the load (e.g., weight) can be adjusted manually with buttons 614.

Figure 7A:
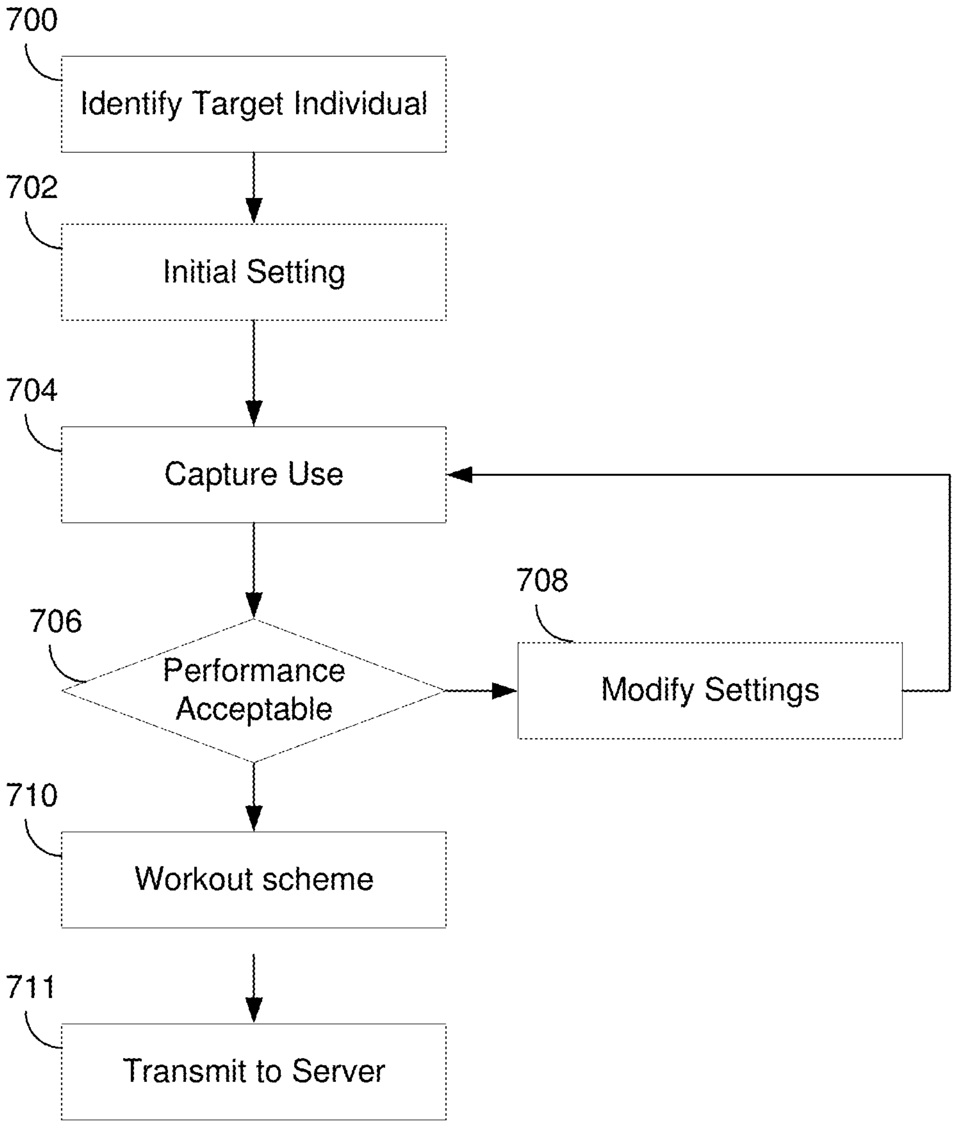
FIG. 7A is a flow chart of aspects of the present system.

Referring to FIG. 7A, components and the processes of the present system are shown in further detail. At 700 a target individual can be identified to use the system for any number of reasons with a number of goals. The target individual may need to improve the current level of physical performance according to a standard such as law enforcement, military, or another standard. The target individual may need to have or improve to a certain level of performance that is anticipated to be needed for a mission or to be mission ready. The target individual may need to be rehabilitated due to some cause such as injury in the field, training, or other reason. In one application, the system can be used to determine an evaluation of the target individual and provide an initial workout scheme.

The initial workout scheme can be a suggested scheme or actual scheme. High performance professionals (e.g., special operations) can use the evaluation system to assess the target individual's current and ideal levels and asymmetries. At 702 the initial settings can be established according to the current state of the target individual and the goals. The initial settings may be generated from information on the target individual's current strength levels, body mass, injury state, and other known health and performance information. Further, the system can access a database of prior target individuals and retrieve initial setting from target individuals that had similar characteristics (e.g., age, weight, gender, strength, injuries, and the like). The target individual can then use the machine with the initial settings and the data is captured at 704. In the event that the initial setting results in inadequate performance (e.g., the load was too high) a determination can be made at 706 and the setting can be modified at 708. If the performance is acceptable, the system generates a baseline evaluation where the workout scheme and rehabilitation plan begin at 710. The information, including the initial workout scheme can be transmitted to a server at 711. Information and inputs can be transmitted to and from the system from a remote device during the process. Further, the remote device can be used to monitor the activity of the system and the target individual during the process. Further, the remote device can be used to develop a set of potential team members for a specific mission where the mission requirements can assist in the determination of the team election (e.g., runners, strength and the like).

Figure 7B:
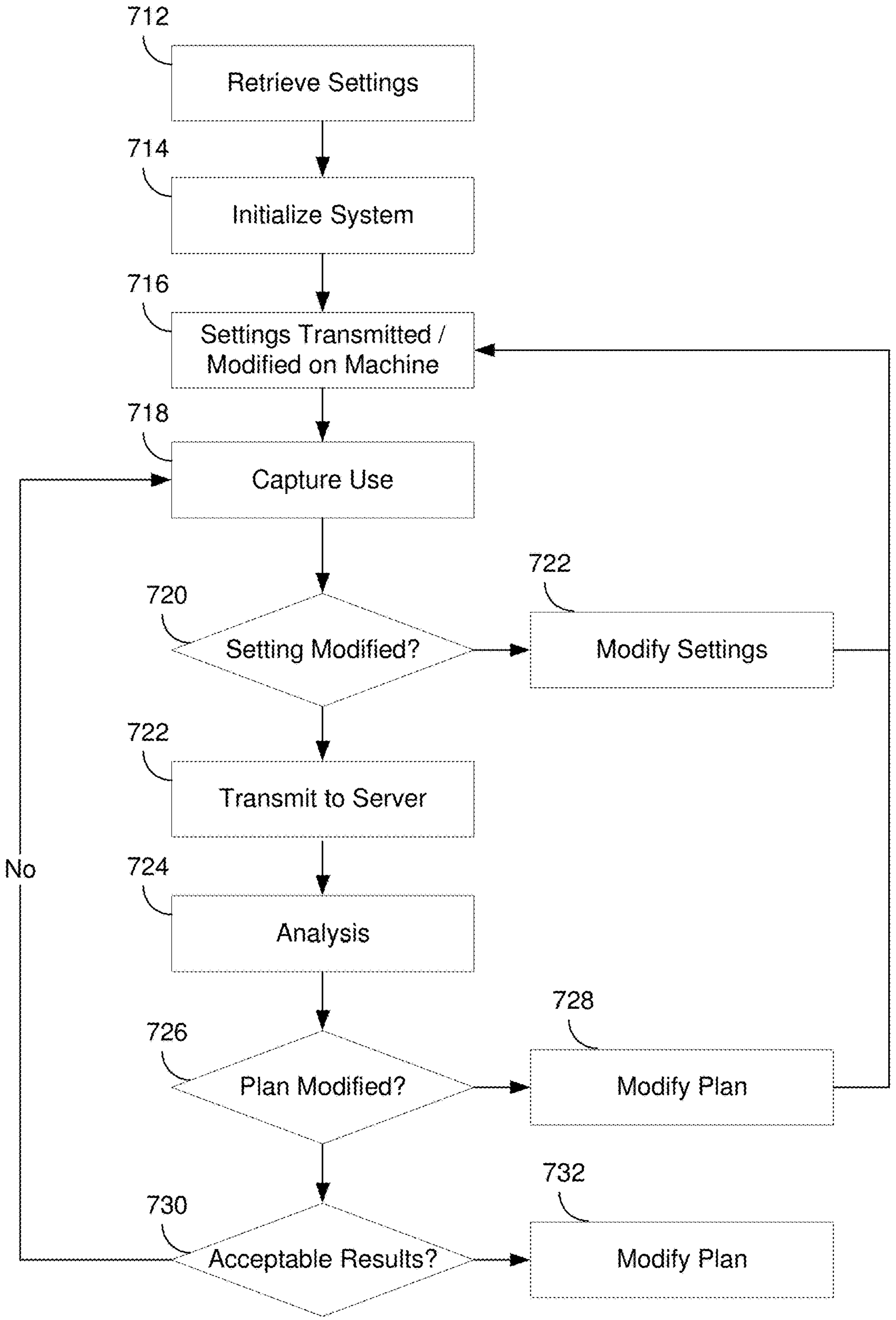
FIG. 7B is a flow chart of aspects of the present system.

Referring to FIG. 7B, the system can be used to facilitate and continue the rehabilitation and workout scheme. The most recent settings are retrieved at 712 and the machine is initialized according to these settings at 714. The target individual can then use the machine at 718 and information from such use can be gathered. When the target individual uses a machine, the target individual information can be associated with that session. The controller can receive a target individual identification that can be alpha-numeric or other information and can include features such as keycard, fingerprint, facial recognition, alphanumeric code, and the like for signing on to the machine and session. Once the target individual signs in, the setting and the hardware and equipment configuration can be set, including seat, resistance, display format, position of components of the equipment and the like.

In one embodiment, a determination can be made based upon the gathered information, whether the settings need to be modified for the next repetition at 720. If so, the modifications are made at 722. Variation in the modifications can include progressive load modifications, static load modification between sessions, or any combination. The user of the machine can be transmitted to one or more servers at 722.

The server can include computer readable instructions that analyze the information gathered at 724, determine if modifications to the workout scheme and/or rehabilitation plan are needed at 726 and if so, modify the workout scheme and/or rehabilitation plan at 728 for the next set, next session, next iteration, and the like for the target individual.

The system can be used for one or more training or rehabilitation plans and can include one or more machines and the initial setting for the one or more machines. For example, a leg press machine can be selected for an evaluation of lower body performance and the workout/rehabilitation plan can include an initial resistance setting for that target individual. In one embodiment, if the results from the target individual are acceptable at 730 the training can be ended at 732.

Computer readable instructions can be included in the controller, server, aggregate servers, or portable device that can be configured to determine and display and report information using the gathered data from assessments and training sessions. The computer readable instructions can determine information described herein (e.g., resistance, velocity, force, power and the like) which can be displayed as a plot on a display or remote device. The results from the system can be used to create a load-velocity profile and power curve that can be associated with a target individual, exercise machine, quadrant of the body, limbs of the body, groups of muscles, date, time, repetition, set, session and the like. In calculating the velocity, the following equation can be used:

$$v = \frac{d}{t}$$

where v is the velocity, d is the change in distance and t is the change in time so that velocity is calculated by determining the distance that the foot pedal traveled and determine a period of time when the foot pedal traveled from an initial position to a final position and can be measured in length units per time units. The computer readable instructions can also calculate the force that is applied by the target individual. The force can be represented by the following equation:

$$F = m * a$$

where F is the force, m is the mass and a is the acceleration. The mass can be determined by translating the resistance into mass and the acceleration can be determined by the following equation:

$$a = \frac{\Delta v}{\Delta t}$$

where α is acceleration, Δv is the change in velocity over the change in time, Δt. The computer readable instructions can determine power from the following equation:

$$P = \frac{W}{\Delta t}$$

where power P is calculated by diving work, W, in the change in time Δt. Work can be calculated by the following equation:

$$W = Fs$$

where work, W can be calculated from force times displacement wherein displacement s represents the change in the position of the foot pedal. In the example, of a foot pedal, the displacement can be the arc that the foot pedal travels around the pivot as well as the line between the starting point and the ending point. The computer readable instructions can generate the power curve by determining the power, such as in watts, over the course of several repetitions performed at different load intensities.

This system allows for the use of bilateral and unilateral strength and power tests to measure left and right limbs performing repetitions at the same time or completely independently. The system can analyze data from strength and power assessments to make comparisons between current and ideal levels of strength, peak power, and power velocity and each of these measurements can be identified for each limb and body quadrant (e.g., lower push, lower pull, upper push, upper pull, core). Differentials (differences in performance between limbs) can be calculated for strength, peak power, power velocity and averages can be calculated across multiple data points. Because the system allows for bilateral activity and measurements, the system can provide limb symmetry improvements to reduce injury risk. The system can also provide for strength symmetry improvements across all quadrants to reduce injury risk, increase current strength levels to goals (e.g., ideal) levels, attain peak power symmetry across all quadrants, increase current peak power levels to ideal levels, attain power velocity symmetry across all quadrants and increase current power velocity levels to ideal levels. These benefits through the structure and function of the system enhances the ability to improve, maintain and rehabilitate physical performance.

In one embodiment, a target individual can be evaluated to determine how their current strength measurements compare to the ideal strength measurements for their specific characteristics (age, gender, weight, specialty, etc.). The evaluation as generally described in FIG. 7A provides baseline metrics that can be used to create training programs aimed at improving strength and power levels as well as limb symmetry. Data from training sessions is continually collected and analyzed in order to make appropriate changes to the exercise prescription based off of their performance. As a target individual uses the system, more data is collected, and that system can provide better predictive analytics. Therefore, the target individual benefits from an improved data set and the system can employ machine learning to better develop recommendations for a performance training plan as well as continually modify the training plan itself.

The system can also use characteristics of the target individual, determine datasets that are from target individuals with similar characteristics and provide estimated or initial treatment plans for the new target individual. Therefore, the system can use machine learning to develop estimated initial performance training plans from historical data collected. As the system develops these initial performance training plans and presents these to the trainer or practitioner, the system can receive modifications to the initial plans. These modifications can be used to inform and modify subsequent performance training plans. For example, if an initial performance training plan is developed for a target individual with certain characteristics and sets an initial load at X, the practitioner may modify this load to Y. Therefore, if the modifications occur routinely, or for a certain target individual, the system can provide subsequent treatment plans with the load of Y, learning from the modifications of the practitioner.

The system can also learn from the performance of one or more target individuals so that during a performance training plan, the system can suggest incremental load increases or other modifications to the plan during the implementation of the training plan. As target individuals improve, the performance training plans with greater results can be used to provide suggestions to subsequent treatment plans.

In one embodiment, the sensors and controller includes an output of data without calculations. In this case, the controller serves as a data source for computer readable instructions that can be disposed locally or remote to the equipment.

Figure 8A:
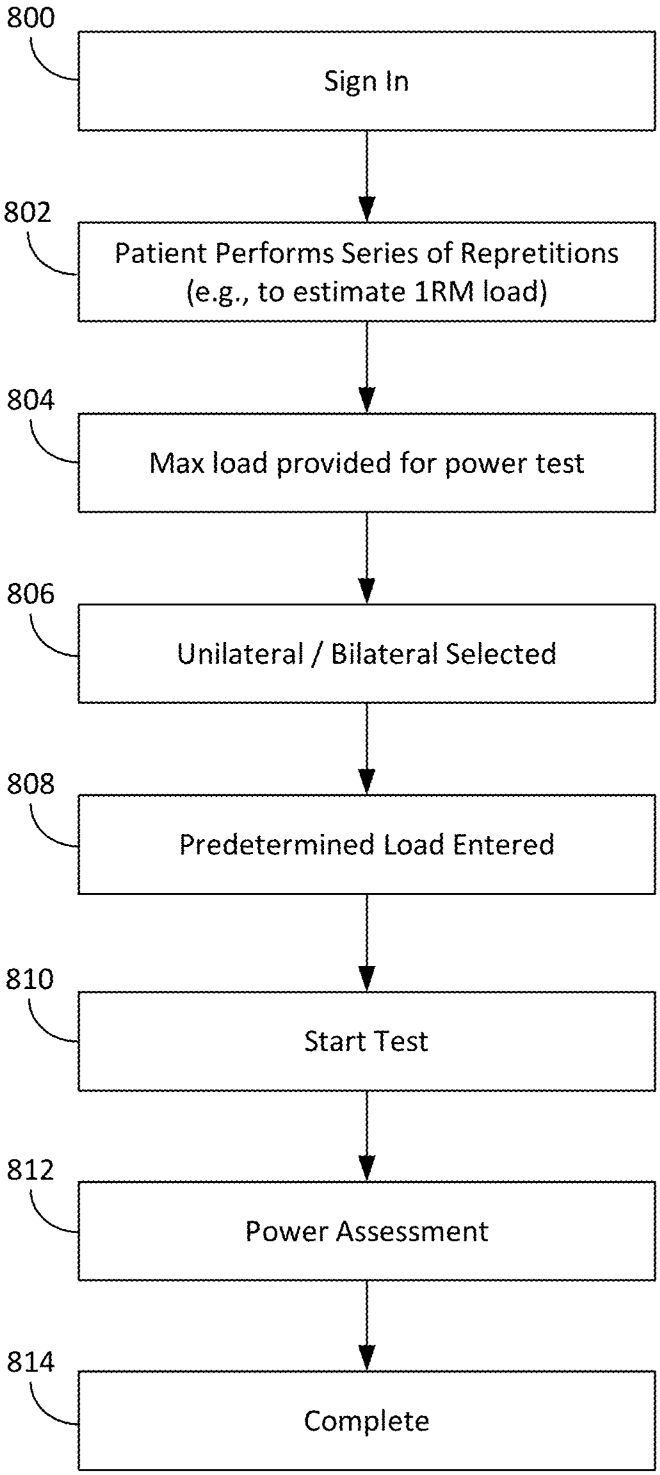
FIG. 8A is a flow chart of aspects of the present system.

Referring to FIG. 8A, the computer readable instructions can determine a strength and power assessment for the patient using one or more machines. The patient or assisting individual can sign in which can include identification information, de-identified information, biometric information, each of which can be unique that can be received by the controller at 800. The system can perform a warm-up phase with the machine and then perform a series of repetitions to determine an estimated one repetition maximum (1RM) at 802. 1RM can represent the most load or resistance that can be performed by the patient with maximum effort from the patient in a single repetition. The system can predict the 1RM using methods such as multiple repetition maximum assessments, load-velocity analyses, and historical patient data or aggregate patient data or the like. For example, using the multiple repetition maximum method, the patient can work up to a heavy load and have them perform as many repetitions as possible. The system can then use that load, number of reps, and/or velocity to estimate what their one repetition max would be. This information can be used to identify current strength levels and any of these processes can be completed on both limbs at the same time or on each limb individually.

According to the patient information that is provided to or retrieved from the controller using one of the methods above for determining an estimated 1RM, a load is determined for the power test at 804. In one embodiment, the health care assistant, trainer or practitioner can choose to run the power test up to a maximal strength load (1RM) or they may choose to run the test at a lower or higher load depending on the capabilities of the patient and the recommendations of the computer readable instructions. With the collection of data, the aggregate dataset can also allow the system to provide an estimation based on the dataset. The system can also use characteristics of the patient, determine datasets that are from patients with similar characteristics and provide estimated or initial treatment plans for the new patient.

Therefore, the system can use machine learning to develop initial power test loads from historical data collected. As the system develops these initial power test loads and presents these to the health care assistant, trainer or practitioner, the system can receive modifications to the initial plans. These modifications can be used to provide subsequent evaluation plans. For example, if an initial evaluation plan is developed for a patient with certain characteristics and sets an initial load at X, the health care provider may modify this load to Y. Therefore, if the modifications occur routinely, or for a certain patient, the system can provide subsequent evaluation plans with the load of Y, learning from the modifications of the health care provider.

Figure 8B:
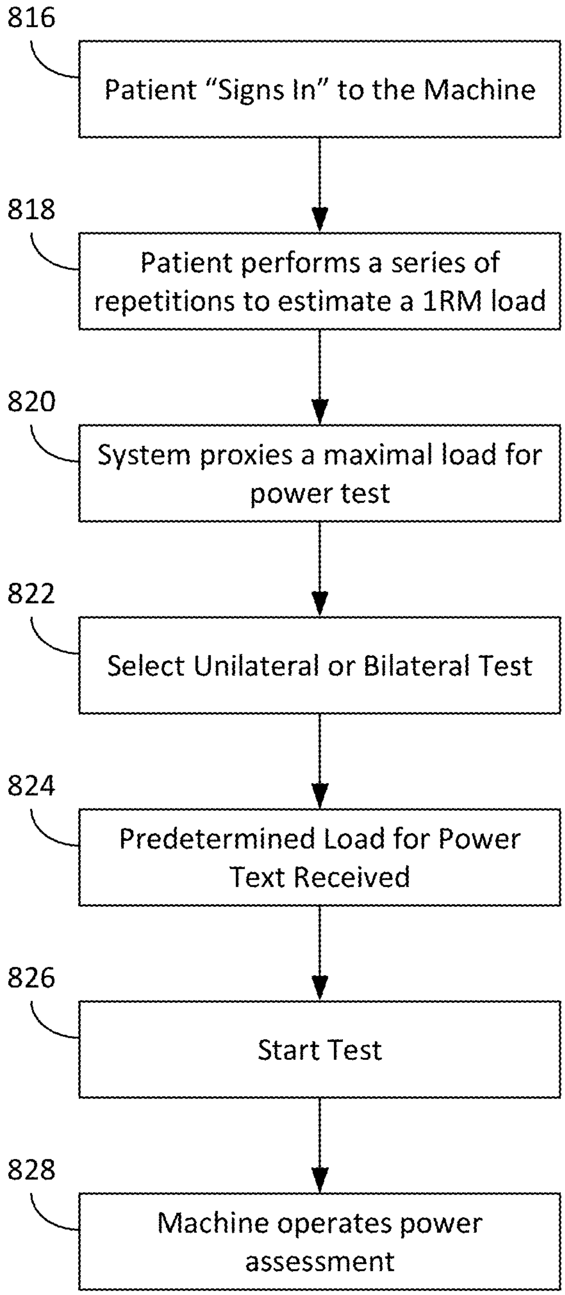
FIG. 8B is a flow chart of aspects of the present system.

Referring to FIG. 8B, the computer readable instructions can also determine a strength and power assessment for the target individual using one or more machines. The target individual or assisting individual can sign in which can include identification information, de-identified information, biometric information, each of which can be unique that can be received by the controller at 816. The system can perform a warm-up phase with the machine and then perform a series of repetitions to determine an estimated one repetition maximum (1RM) at 818. 1RM can represent the most load or resistance that can be performed by the individual with maximum effort from the individual in a single repetition. The system can predict the 1RM using several methods such as multiple repetition maximum assessments, load-velocity analyses, a database of tactical athlete data or similar data or the like. For example, using the multiple repetition maximum method, the individual can work up to a heavy load and have them perform as many repetitions as possible. The system can then use that load, number of reps, and/or velocity to estimate what their one repetition max would be. This information can be used to identify current strength levels and any of these processes can be completed on both limbs at the same time or on each limb individually.

According to the individual's information that is provided to or retrieved from the controller using one of the methods above for determining an estimated 1RM, a load is determined for the power test at 820. In one embodiment, trainer or practitioner can choose to run the power test up to a maximal strength load (1RM) or they may choose to run the test at a lower or higher load depending on the capabilities of the individual and the recommendations of the computer readable instructions. With the collection of data, the aggregate dataset can also allow the system to provide an estimation based on the dataset.

A power test can include an assessment that takes a target individual through a number of repetitions (e.g., in the range of 5 to 20) of gradually increased resistance leading up to a maximal load (1RM) that was entered into or calculated by the system. This assessment can provide data on velocity, power, force, range of motion, work etc. and generate the data that is shown in the Figures (e.g., FIGS. 9A through 9C) for each limb individually. The target individual or assisting individual can determine if the exercise will be unilateral or bilateral at 806 and provide input to the system, such as the controller, accordingly. A maximal load (1RM), or estimated maximal load, can be entered into the system. The maximal load can be used to determine the repetition loads that will gradually increase as determined by the computer readable instructions. The controller is provided with the load or resistance at 808, the test starts at 826 and the target individual particulates in the exercise at 828 until the test is complete. In one example, the target individual can complete one repetition at a time as fast as possible and then receives a rest period before completing the next rep. This example can be used to take the target individual through several repetitions of a gradually increasing load leading up to the resistance that was entered or until the practitioner ends the assessment. The computer readable instructions can also determine the increase in the load according to a predetermined protocol or according to the real-time data received from each repetition from the target individual.

The system can also learn from the performance of one or more patients so that during an evaluation, the system can suggest incremental load increases or other modifications to the plan during the implementation of the evaluation. Evaluations with more accurate and reliable data sets can be used to provide suggestions for subsequent evaluation plans.

The data that is gathered during this power test is transmitted to one or more computer systems, locally or remotely. The computer system can receive data from other systems including healthcare provider systems. For example, patient criteria can be received from the medical record of the patient and can be used for the initial evaluation as well as the subsequent workout scheme and rehabilitation. The assessment data can be associated with the patient record and can also be associated with each type of activity, exercise and machine including leg press, chest press, leg curl, upper row, other machines and any combination. A maximal load for each test can be received or calculated from this information as well as power velocity, peak power and other data points that can be received and used by the system for each limb.

In one embodiment, and according to the individual's information that is provided to or retrieved from the controller using one of the methods above for determining an estimated 1RM, a load is determined for the power test at 804. In one embodiment, trainer or practitioner can choose to run the power test up to a maximal strength load (1RM) or they may choose to run the test at a lower or higher load depending on the capabilities of the individual and the recommendations of the computer readable instructions. With the collection of data, the aggregate dataset can also allow the system to provide an estimation based on the dataset.

A power test can include an assessment that takes a target individual through a number of repetitions (e.g., in the range of 5 to 20) of gradually increased resistance leading up to a maximal load (1RM) that was entered into or calculated by the system. This assessment can provide data on velocity, power, force, range of motion, work etc. and generate the data that is shown in the Figures (e.g., FIGS. 9A through 9C) for each limb individually. The target individual or assisting individual can determine if the exercise will be unilateral or bilateral at 806 and provide input to the system, such as the controller, accordingly. A maximal load (1RM), or estimated maximal load, can be entered into the system. The maximal load can be used to determine the repetition loads that will gradually increase as determined by the computer readable instructions. The controller is provided with the load or resistance at 808, the test starts at 810 and the target individual particulates in the exercise at 812 until the test is complete at 814. In one example, the target individual can complete one repetition at a time as fast as possible and then receives a rest period before completing the next rep. This example can be used to take the target individual through several repetitions of a gradually increasing load leading up to the resistance that was entered or until the practitioner ends the assessment. The computer readable instructions can also determine the increase in the load according to a predetermined protocol or according to the real-time data received from each repetition from the target individual.

The data that is gathered during this power test is transmitted to one or more computer systems, locally or remotely. The computer system can receive data from other systems including healthcare provider systems. For example, target individual criteria can be received from the medical records or training records of the target individual and can be used for the initial evaluation as well as the subsequent training scheme and/or rehabilitation. The assessment data can be associated with the target individual record and can be also associated with each type of activity, exercise and machine including leg press, chest press, deadlift, upper row, core rotation, leg curl and other machines and any combination. A maximal load for each test can be received or calculated from this information as well as power velocity, peak power and other data points that can be received and used by the system for each limb.

The system and the computer readable instructions can evaluate the power test completed on one or both limbs. In one embodiment, the data from the series of repetition completed within a power assessment can be plotted. The variables included in the plots can be velocity, power, resistance, force, and the like.

Figure 9A:
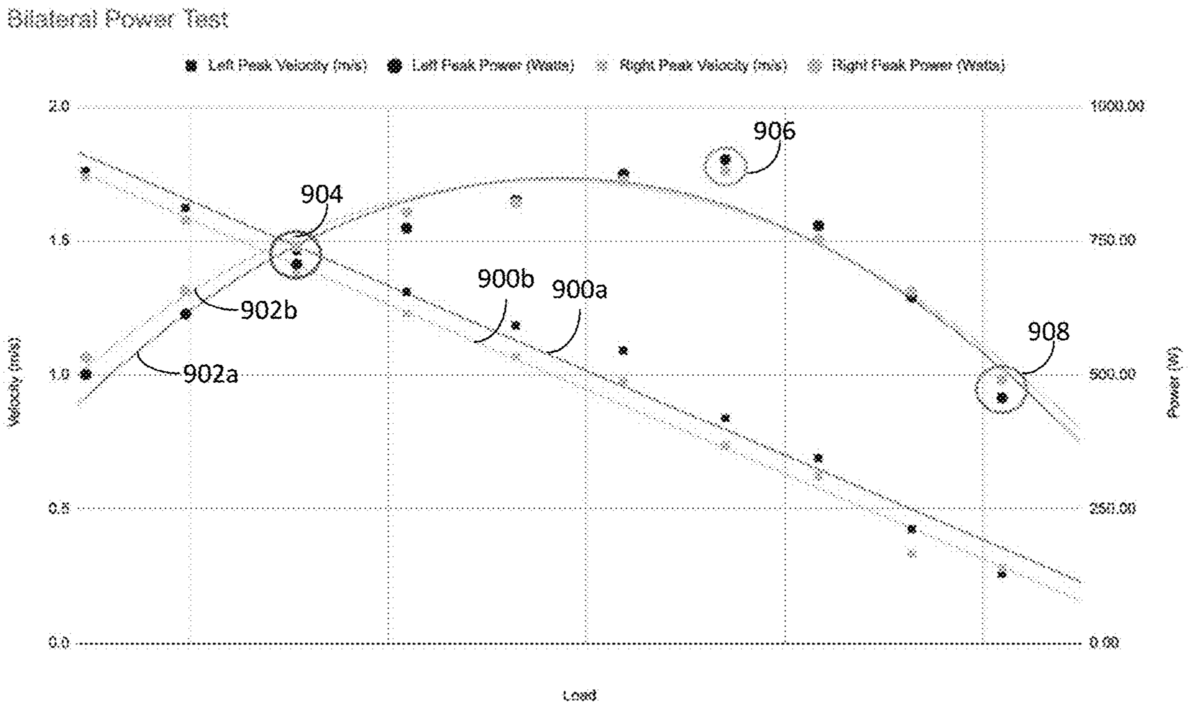
FIG. 9A is a graphical representation of aspects of the present system.

Referring to FIG. 9A, the data that is collected from the assessment is shown. The velocity (e.g., meters per second) of the left limb is shown as 900*a* and the right limb as 900*b*. The power (e.g., Watts) for the left limb is shown as 902*a* and the right limb as 902*b*. In one embodiment the lines of best fit can be determined for the left and right limbs' force-velocity relationship shown below. Further, a best fit analysis can be determined for the left and right limbs' power. Further, the best fit can be determined using data from the power test on that specific leg. This data can also be normalized.

Figure 9B:
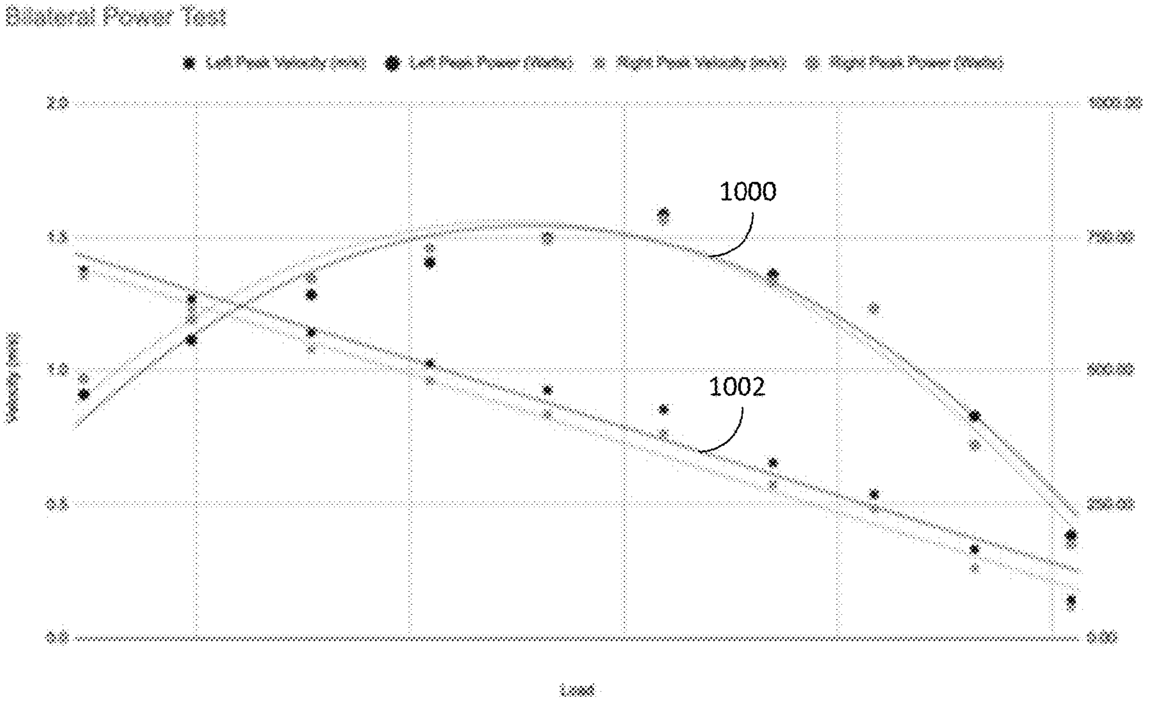
FIG. 9B is a graphical representation of aspects of the present system.
Figure 9C:
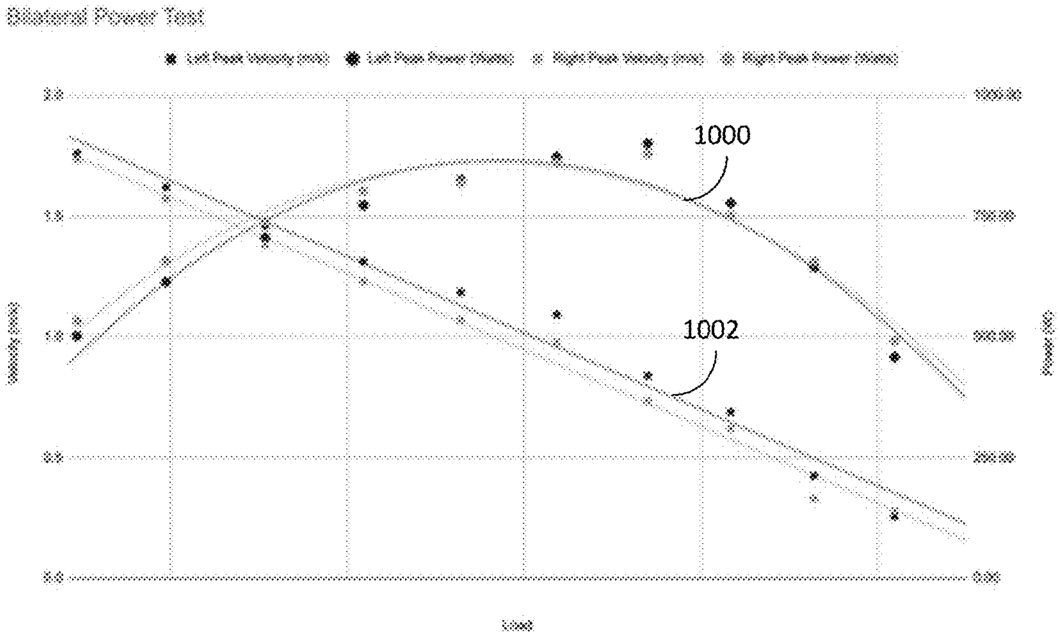
FIG. 9C is a graphical representation of aspects of the present system.

Referring to FIGS. 9B and 9C, examples of graphic representations of some of the performance goals and data readings are shown. In one embodiment, the goal of training can be for high performance and can include the goal of maximizing strength, peak power, and power velocity levels while minimizing asymmetries between limbs and quadrants (e.g., upper push, lower push, upper pull, lower pull). The system allows for the performance to be measured against these goals and provides data used to increase the maximal load and then increase the power and velocity at every load, thereby moving the power curve(s) 1000 and velocity line(s) up 1002 and to the right. The system allows for training based on the target individual evaluation, needs analysis (sport, position, energy system demands), schedule and available time.

The system can determine a line of best fit for left and right force-velocity relationships 900*a* and 900*b* respectively with the following equation being an example of the computer readable instructions process and operation:

$$y=mx+b$$

where y is the y-axis, m is the slope, x is the x-axis and b is the y intercept of a straight line.

The system can determine the line of best fit for left and right power relationships represented by the curves 902*a* and 902*b*. The best fit of the power curve can be determined by several methods including the following that can be implemented in computer readable instructions as an example:

$$y = Ax\string^2 + Bx + C$$

where y is the dependent variable, x is the independent variable, a is a coefficient, b is a coefficient, and c is a coefficient. Any number of methods can be used for the best fit and can include generating one line that minimizes the distance between the line and the gathered data for each limb. Therefore, this graph can show all power data and are not specific to peak power or power velocity and these points can be determined from the line(s). The data can be analyzed by the individual data points as well as any part of each line of best fit (for each limb). The differences between limbs at any one point or across several points can be calculated as bilateral differentials.

Peak power and power velocity can be represented by two points determined from the test data of each limb. These points can be visually determined from plotting the data and/or numerically defined from an algorithm. The value that is used for calculating the power velocity point and the power velocity bilateral differential can be in a range that can include point 904 where the power line and the velocity line intersect. These points can be determined from each leg individually (e.g., right leg power velocity and left leg power velocity). The power velocity points can have a corresponding force, load, average wattage, peak wattage, average velocity, and peak velocity and the like. The peak power and peak power bilateral differential can be calculated at 906 which can be the highest data point of power output. The peak power and peak power bilateral differential could also be calculated from the highest point of the power curve (line of best fit). These points can be determined from each leg individually (e.g., right leg peak power and left leg peak power). The peak power point can have a corresponding force, load, average wattage, peak wattage, average velocity, and peak velocity and the like. The maximal load can be calculated from the maximal exertion assessment, at 908 where the last successful repetition performed by the target individual occurs, or can be estimated based on the dataset. These points can be determined from each leg individually (e.g., right leg maximal load and left leg maximal load) or both legs together. The maximal load point can have a corresponding force, load, average wattage, peak wattage, average velocity, and peak velocity and the like. The system can provide and display strength, peak power and power velocity data as this data can be identified and compared between tests completed at different points in time. The power velocity, peak power, and maximal load points can be used to determine current performance levels, difference from ideal levels, appropriate training loads, as well as provide an assessment of potential injury risk.

In one embodiment, the average power bilateral differential can be calculated by averaging the repetitions occurring at loads involving high velocities and lesser forces. The average strength bilateral differential can be calculated from the repetitions involving lower velocities and higher forces. An overall differential may also be calculated by averaging the differences in limb performance across all successful repetitions. The computer readable instructions can perform the following processes represented as:

$$Ave = \frac{\sum_{i=1}^{n} r_i}{n}$$

where c is the average of the successful repetition, n is the number of success repetitions and r is the value of the corresponding repetition.

During an evaluation, which can be an entire body evaluation, of a healthy individual, current values can be measured for strength, peak power, power velocity and bilateral differentials for each quadrant (e.g., lower push, lower pull, upper push, upper pull, core). The target individual's ideal values could be calculated for each of these metrics within each quadrant. Comparisons can be made between current and ideal values for all metrics. Ideal values can be aspirational goals, pre-injury levels, performance levels, rehabilitation levels and the like. The target individual would be evaluated on strength levels, strength symmetry, strength symmetry variance, average strength bilateral differential, peak power levels, peak power symmetry, peak power symmetry variance, peak power bilateral differential, average power bilateral differential, power velocity levels, power velocity symmetry, power velocity symmetry variance, power velocity bilateral differential, and average power bilateral differential. The target individual's training program would then be developed based on the information from their evaluation.

In the case that the machine is the leg press, strength can be calculated for both limbs and for each limb separately. In one embodiment, the system can identify the strength levels including the current level as well as an ideal level. The ideal levels can be calculated based upon the specific characteristics of the target individual such as gender and body weight so that the ideal levels are individually and specifically calculated for each target individual. Specific target individual characteristics can include age, gender, weight, height, injury status, medical history, occupational specialties, and the like.

In one embodiment, current strength can be the estimated 1RM from the final repetition completed during the power test. . . . The system can determine the current strength level of both legs or each leg individually, ideal strength level of both legs or each leg individually, and bilateral differentials (e.g., difference between legs across one or more repetitions). This information can be displayed in a graphical format. For example, a male target individual's ideal bilateral leg press may be a factor of (such as four times) the target individual's body weight. Different calculations for ideal strength and power levels exist for each piece of exercise equipment in combination with the target individual's characteristics. In addition, ideal levels for peak power and power velocity can be determined based on a percentage of ideal strength according to the exercise machine or body quadrant.

The system can also determine the current and ideal peak power levels of both limbs and each limb independently. For example, if the target individual's ideal strength for leg press is 400 pounds, then the target individual's ideal Peak Power level could be 75% of that ideal strength level (i.e., 300 lbs.). The system can also determine bilateral differentials at peak power.

The system can also determine the current and ideal power velocity levels of both legs and each leg individually. For example, if the target individual's ideal strength for leg press is 400 pounds, then the target individual's ideal Power Velocity level could be 55% of that ideal strength level (i.e., 220 lbs.). The system can also determine bilateral differentials at power velocity.

The system can provide and display strength, peak power and power velocity, and bilateral differential data as this data can be identified for each specific quadrant and compared between tests completed at different points in time. These values, strength, peak power, and power velocity can be determined for various machines representing different parts of the target individual and can include use of leg press, chest press, deadlift, upper row, core rotation, leg curl, latissimus dorsi (lat.) pulldowns, military presses, leg extensions, other work out machines and any combination.

In the case of evaluating a target individual's performance these performance measures (maximal strength, peak power, power velocity, and bilateral differentials) can be identified from unilateral or bilateral power tests depending on the protocol. These points can include data on force, load, velocity, wattage, range of motion and others. These points can provide markers for comparison and interpretation. For tactical target individuals, the system can assist with bringing their current levels (strength, peak power, and power velocity) up to their ideal levels. Additionally, the system can assist with achieving symmetrical performance between the quadrants and limbs, which may assist with injury risk reduction. Therefore, this system can assist the target individual to maximize their own performance without assistance from a trainer, or the like.

Each machine that can be used by the target individual can be used in communications with the system and follow the same processes and functionality provided by the system as described where with each machine having the ability to provide its own set of data. In one embodiment, ideal strength, peak power and power velocity levels can differ per machine. In one embodiment, the target individual's current and ideal values (e.g., strength, peak power, power velocity, etc.) can be determined for each machine regardless of what machine is used.

In one embodiment, if evaluations are completed on more than one machine, the system can calculate a multi-quadrant evaluation of the target individual. For example, these assessments, evaluations, and calculations can be determined for the right side above the waist, right side below the waist, left side above the waist, left side below the waist and any combination as well as left and right-side core (trunk). These assessments, evaluation and calculations can be determined for the right arm, left arm, right leg and left leg, right core and left core and any combination. The system can also further evaluate performance within a single limb or area of the body by comparing multiple assessments of specific muscle groups (i.e. quadriceps v. hamstrings).

From these evaluations, performance training plans can be created or modified. According to the evaluation and assessment, the performance training program can be determined for each quadrant and for each machine or exercise. For example, in the case that the target individual has a weaker left leg than right leg, an occurrence that can result from an injury or can be an indicator of future injury, the system can design a training plan that includes an appropriate loading protocol to rehabilitate the weaker leg to the same strength level of the stronger leg as well as improve the strength bilateral differential. The system can also design a performance training plan that improves strength levels and strength symmetry (strength comparisons across body quadrants, e.g., lower push and lower pull strength) and reduces variance across multiple machines. For example, if a target individual's lower pull performance (as measured by the deadlift) is 20% below their ideal strength and the other quadrants are all close to ideal (<5%) then the performance training program will be specifically targeted to improve the quadrant symmetry as this will reduce potential injury risk. The system can also create and/or modify a performance training plan that seeks to improve peak power performance of specific machines/quadrants as well as increasing peak power symmetry and reducing variance across multiple machines/quadrants. The system can also create and/or modify a performance training plan that seeks to improve power velocity performance of specific machines/quadrants as well as increasing power velocity symmetry and reducing variance across multiple machines/quadrants. The system can create and/or modify performance training programs that target reducing bilateral differentials (asymmetries in limb performance) by training specific decrements in strength and/or power performance on one limb. The system can create individualized training programs that address any combination of the above mentioned goals. The system may also include non-machine specific training elements such as motor skill exercises, mobility training, resistance training, plyometric training, cardiovascular training and the like.

When a target individual is using the system, the system can learn from the target individual's use and gather data so that the training protocol can change over time and be specific to that target individual. One example would include a target individual completing an evaluation and having a large peak power deficit in one quadrant (i.e., lower pull) which leads to a poor peak power symmetry score. The system would prescribe a training program targeted at improving peak power symmetry. The system can then take a stair-stepper approach to monitoring power output and increasing load until the peak power symmetry reaches a specific threshold. Once the desired target is reached, the system can alter the training to generate a more symmetrical prescription for performance enhancement. This process can be autoregulated by the computer based on real-time training data so that the training programs are always specific to the individuals current performance without having to rely on a subsequent evaluation to alter the protocol.

For example, if the target individual is prescribed a training program for a lower pull peak power deficit, the loads and wattages of their lower pull exercise will be monitored for improvement. During a training session if they exceed their previous wattage by more than 10%, the computer can automatically adjust their resistance to a higher load. While the progression is determined by the target individual's progress and the computer readable instructions learning from the process, an illustrative example of the process is shown below.

The system can include the functionality of determining that peak power production for the lower pull quadrant is 100 lbs., which can be 10% less for the lower pull quadrant compared to the lower push quadrant. Although all quadrants may need to improve, the lower pull quadrant needs to take priority to improve overall symmetry. With this information the following can be prescribed by the system:

Week 1:

- Leg Press: 2 sets of 6 repetitions at peak power load
- Chest Press: 2 sets of 6 repetitions at peak power load
- Deadlift: 3 sets of 6 repetitions at peak power load (100 lbs.), 2 sets of 6 repetitions at 105 lbs., 2 sets of 4 repetitions at 110 lbs.
- Upper Row: 2 sets of 6 repetitions at peak power load Week 2:

- Leg Press: 2 sets of 6 repetitions at peak power load
- Chest Press: 2 sets of 6 repetitions at peak power load
- Deadlift: 3 sets of 6 repetitions at peak power load (105 lbs.), 2 sets of 6 repetitions at 110 lbs., 2 sets of 4 repetitions at 115 lbs.
- Upper Row: 2 sets of 6 repetitions at peak power load As can be seen, the system allows for specific training prescriptions which target the deficits identified during the evaluation.

The computer readable instructions can develop a training plan designed to enhance performance by improving strength and power levels and improving symmetry across quadrants and limbs. For example, in tactical target individuals, and to describe the goals graphically, the training plan can be designed to bring the power levels of one or more quadrants up to the ideal levels by seeking to increase the velocity and power output of their movements. Using the training programs, data from the equipment, exercises, and the continuing modifications of the training plan, neuroplasticity in the target individual can be improved, physical performance can be improved, injury risk can be lowered, and the recovery time in injured target individuals can be improved. By assessing both limbs (either at the same time or with separate assessments), a customized initial performance baseline for the particular target individual can be established as the system can determine the strength, peak power, and power velocity of each limb in each quadrant. Further, as the target individual and system interact, the system can monitor the improvements of both limbs and all quadrants so that as performance improves, the relative improvement of each limb and each quadrant are appropriately adjusted within the training program to maintain or promote improvements in symmetry. Further, in the event that a target individual were to experience an injury, the system can detect the reduction in performance and automatically adjust the programming accordingly.

In one embodiment, once the assessment is performed and the baseline of performance established according to the current and ideal levels of the target individual, the performance training program is created with the goal of reducing limb and quadrant asymmetries and improving strength and power to the ideal levels.

Referring to FIG. 9B, one embodiment shows pre-training graphical results of an assessment and evaluation of one quadrant of a target individual. FIG. 9C shows the post-training graphical results of an assessment and evaluation of the same quadrant. You can see that the velocities and power outputs are generally higher in FIG. 9C compared to FIG. 9B. You can also see that the points at which power velocity and peak power occur to have higher power output and occur at higher resistances in FIG. 9C. This represents improved neuromuscular performance that would translate to improve physical performance in tactical operations.

Figure 10A:
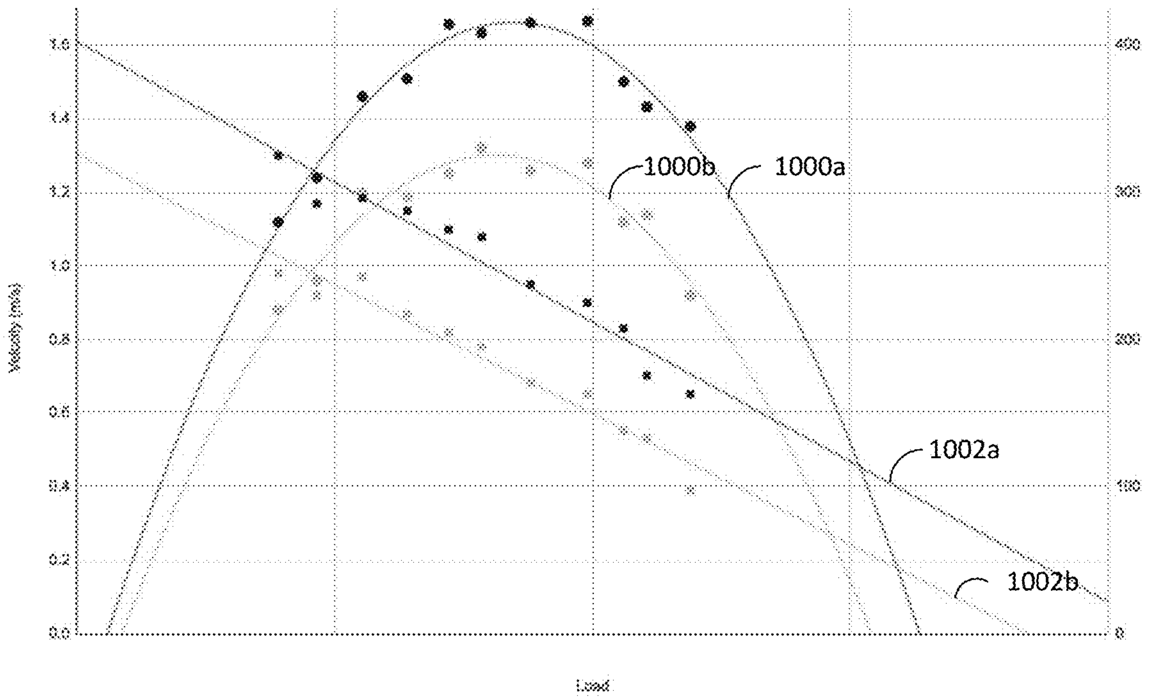
FIG. 10A is a graphical representation of aspects of the present system.
Figure 10B:
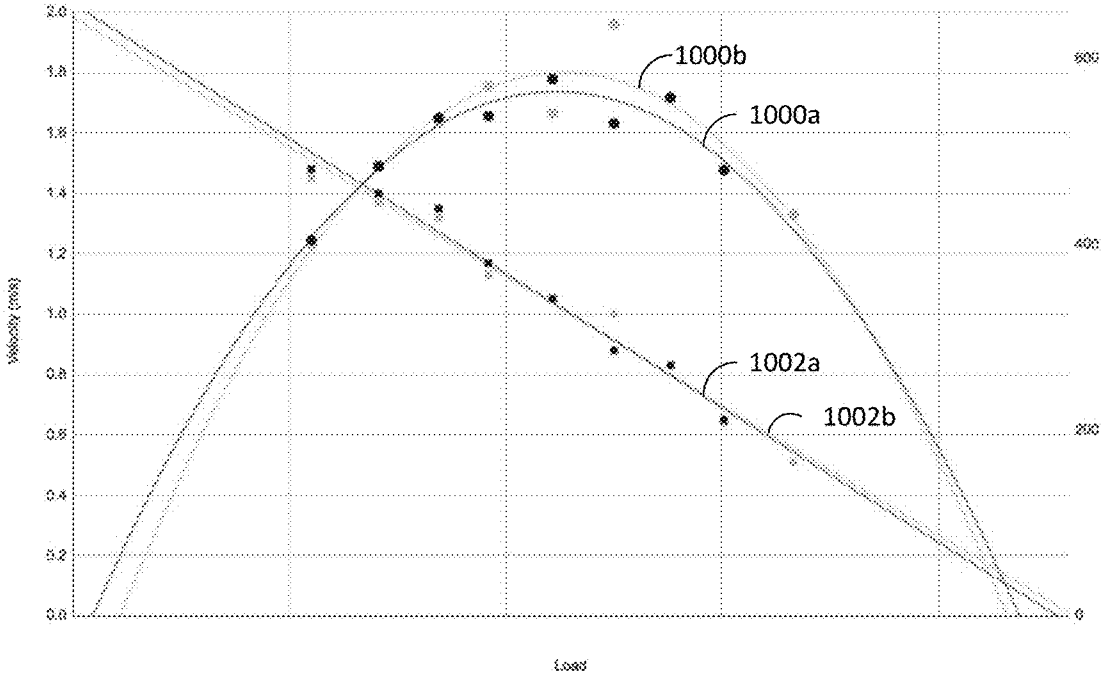
FIG. 10B is a graphical representation of aspects of the present system.

Referring to FIGS. 10A and 10B, the baseline of performance 1000*a* is shown with values provided for illustrative purposes. The values can vary from individual to individual and purpose to purpose. The value can be determined from the historical information that is collected from the target individual using the system. For example, in the case of the injured target individual, the target curve 1000*a* can be based upon prior performance of that individual. The target curve 1000*a* can also be representative of physical performance that is desired by the target individual. The target curve 1000*a* can be the physical requirements that are anticipated to be needed for a mission. The target curve 1000*a* can be the physical performance that was needed from experience (e.g., missions). In one embodiment, the target performance 1000*a* can be based upon similar other individuals with the goal of having the target individual increase the performance to that of the other individuals. In one embodiment the baseline can be the performance that is desired according to mission parameters (e.g., strength, endurance or other traits or combination of traits). In one embodiment, the load applied to the target individual can represent the physical stresses on the target individual in reality or anticipated (e.g., mission parameters) such as ruck sack weight and the like.

In one embodiment, the system provides real-time biofeedback for the target individual to see their performance of every repetition. This allows for maximal voluntary effort. In another embodiment, the performance training plan can include additional processes and equipment including surface muscle stimulation or transcranial magnetic stimulation which can improve and accelerate the regeneration of neural pathways, particularly after an injury. Electrical stimulation can elicit greater nervous system recruitment by activating motor neurons that may currently be inhibited under voluntary activation. For example, electrical stimulation may be used on a target individual's quadricep when completing their leg press exercise. This would allow them to produce more force and velocity. The system can use electrical stimulation (such as with surface EMG or transcranial magnetic stimulation) that can activate involuntary neural responses to cause greater neural output than voluntary alone.

A performance training plan can be created based on information from their performance evaluation as well as other training, task, and medical information (e.g., previous training metrics, mission-related tasks, injury history). A performance training plan can also be developed based upon the performance levels that have historically shown to provide for higher mission success, where the mission can be from graduation from boot camp to elite missions such as insurgence into hostile battle environments. A performance training plan can also be developed based upon one or more mission parameters. A performance training plan can also be developed based upon physical ability and stamina standards associated with the target individual service. For example, the minimum physical ability and stamina standards may be as shown in Table 1:

TABLE 1

| Task | Score (points awarded) |
|---|---|
| Pull-ups 2 minutes | 8 |
| Sit-ups 2 minutes | 50 |

TABLE 1-continued

| Task | Score (points awarded) |
|---|---|
| Push-Ups 2 minutes | 40 |
| 1 mile run | 15 |
| 25-meter underwater swim | Pass/Fail |
| 500-meter swim | 15 |

A target individual may desire to improve on one or more of the above tasks so that the performance plan can be developed that seeks to improve the performance in one of more of the above tasks, while taking into consideration the current performance of the target individual. In some cases, the system can be used to evaluate the target individual so that weaknesses are identified and corrected prior to the point where the physical performance is tested. For example, prior to entering basic training, prior to joining an advanced or elite group, after an injury, to deploy or otherwise engage during a mission of other goal.

Based on the information, the target individual can begin an appropriate exercise protocol that aligns with the collected information. Once exercise protocol is underway the sessions can be automatically adjusted based on performance allowing for a completely individualized plan according to their progress.

It is understood that the above descriptions and illustrations are intended to be illustrative and not restrictive. It is to be understood that changes and variations may be made without departing from the spirit or scope of the following claims. Other embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventor did not consider such subject matter to be part of the disclosed inventive subject matter.

What is claimed is:

1. A system for implementing a dynamic performance enhancing schema comprising:

an exercise machine having a load assembly for applying a load to a limb of a target individual;

a force sensor in electrical communications with the load assembly for detecting a force applied by the limb by the target individual using the exercise machine;

a velocity sensor for receiving velocity information representing a velocity applied by the limb by the target individual using the exercise machine; and, a computer system in communications with the load assembly, the force sensor and the velocity sensor for determining an initial power, receiving load information, receiving a velocity information, receiving a force information, analyzing a power and velocity data, modifying the load applied to the target individual according to the power and velocity data and applying the modified load to the limb of the target individual during a subsequent use of the exercise machine by the target individual, wherein the computer system determines bilateral differentials by comparing power and velocity data between a first limb and a second limb to identify asymmetries and modifies the workout scheme to reduce injury risk based on the bilateral differentials.

2. The system of claim 1 wherein the limb is a first limb, the force sensor is a first force sensor, the velocity sensor is a first velocity sensor and the power and velocity analysis is a first power and velocity analysis and the computer system is adapted to create a work scheme for a second limb according to a second power and velocity analysis derive from a second force sensor and a second velocity sensor.

3. The system of claim 1 wherein the computer system is adapted to determine a performance target according to historical performance information of the target individual according to the power and velocity data analysis.

4. The system of claim 1 wherein the computer system is adapted to determine a performance target according to a set of mission parameters.

5. The system of claim 1 wherein the computer system is adapted to determine a target individual performance goal according to a set of historical mission parameters.

6. The system of claim 1 wherein the computer system is adapted to determine a target individual performance goal according to an individual performance goal.

7. The system of claim 6 wherein the target individual performance goal is a performance standard.

8. The system of claim 1 wherein the computer system is adapted to determine an estimated maximal load.

9. The system of claim 1 wherein the computer system is adapted to determine a peak power and power velocity for each limb independently and calculate bilateral differentials at peak power and power velocity between limbs to identify asymmetries for injury risk reduction.

10. The system of claim 1 wherein the computer system is adapted to determine a workout scheme according to power information, the load information, the velocity information, the force information, the power and velocity analysis and a performance target, wherein the computer system determines peak power and power velocity for each limb independently and calculates bilateral differentials between limbs to identify asymmetries for injury risk reduction.

11. The system of claim 10 wherein the power information is a first power information, the load information is a first load information, the velocity information is a first velocity information, the force information is a first force information and the computer system is adapted to create a second power and velocity analysis according to a second power information, a second load information, a second velocity information, and a second force information received from a subsequent use of the exercise machine by the target individual, wherein the second power and velocity analysis includes determining peak power and power velocity for each limb independently and calculating bilateral differentials between limbs to identify asymmetries for injury risk reduction.

12. The system of claim 1 wherein the computer system is adapted to determine a workout scheme using an iterative process from a set of load information, a set of velocity information, and a set of force information received from the subsequent use of the exercise machine by the target individual.

13. The system of claim 1 wherein the computer system is adapted to determine whether modifications in the load applied to the target individual are repeated for each target individual session.

14. A system for implementing a dynamic performance enhancing schema comprising:

a set of prior user characteristics;

a computer system adapted to receive a set of target individual characteristics and generate an initial workout scheme according to a similarity match of the target individual characteristics and the set of prior user characteristics;

an exercise machine having a load assembly for applying a load to a limb of a target individual according to the initial workout scheme;

a force sensor in electrical communications with the load assembly for detecting a force applied by the limb by the target individual using the exercise machine;

a velocity sensor for receiving velocity information representing a velocity applied by the limb by the target individual using the exercise machine; and, wherein the computer system is in communications with the load assembly, the force sensor and the velocity sensor and adapted for determining power information, receiving load information, receiving a velocity information, receiving a force information, determining a power and velocity analysis, creating a modified workout scheme according to the power and velocity analysis, wherein the computer system determines bilateral differentials by comparing power and velocity data between a first limb and a second limb to identify asymmetries and modifies the workout scheme to reduce injury risk based on the bilateral differentials.

15. The system of claim 14 wherein the modified workout scheme includes a modified load applied to the limb of the target individual during a subsequent use of the exercise machine by the target individual.

16. The system of claim 14 wherein the limb is a first limb, the force sensor is a first force sensor, the velocity sensor is a first velocity sensor, the power and velocity analysis is a first power and velocity analysis and the computer system is adapted to create a workout scheme for a second limb according to a second power and velocity analysis derive from a second force sensor and a second velocity sensor.

17. The system of claim 16 wherein the computer system is adapted to create the workout scheme for a second limb according to workout scheme of the first limb.

18. A system for implementing a dynamic performance enhancing schema comprising:

a computer system adapted to receive a set of target individual characteristics and generate an initial workout scheme according to a set of mission performance parameters;

an exercise machine having a load assembly for applying a load to a limb of a target individual according to the initial workout scheme;

a force sensor in electrical communications with the load assembly for detecting a force applied by the limb by the target individual using the exercise machine;

a velocity sensor for receiving velocity information representing a velocity applied by the limb by the target individual using the exercise machine; and, wherein the computer system is in communications with the load assembly, the force sensor and the velocity sensor and adapted for determining power output, receiving load information, receiving a velocity information, receiving a force information, determining a power and velocity analysis, creating a modified workout scheme according to the power and velocity analysis, wherein the computer system determines bilateral differentials by comparing power and velocity data between a first limb and a second limb to identify asymmetries and modifies the workout scheme to reduce injury risk based on the bilateral differentials.

19. The system of claim 18 wherein the limb is a first limb, and the initial workout scheme is a first initial workout scheme for the first limb and the computer system adapted to generate a second initial workout scheme for a second limb.

20. The system of claim 19 wherein the power and velocity analysis is a first power and velocity analysis for the first limb and the computer system adapted to generate a second power and velocity analysis for the second limb and determine a difference between the first power and velocity analysis and the second power and velocity analysis indicating a difference in performance between limbs.

* * * * *